US008955974B2

(12) United States Patent
Gross et al.

(10) Patent No.: US 8,955,974 B2
(45) Date of Patent: Feb. 17, 2015

(54) SYSTEMS AND METHODS FOR EVALUATING HUMAN EYE TRACKING

(71) Applicant: RightEye, LLC, Potomac, MD (US)

(72) Inventors: Adam Todd Gross, Potomac, MD (US); Melissa Hunfalvay, Silver Spring, MD (US)

(73) Assignee: RightEye, LLC, Potomac, MD (US)

( * ) Notice: Subject to any disclaimer, the term of this patent is extended or adjusted under 35 U.S.C. 154(b) by 0 days.

(21) Appl. No.: 14/490,296

(22) Filed: Sep. 18, 2014

(65) Prior Publication Data

US 2015/0002815 A1    Jan. 1, 2015

Related U.S. Application Data

(63) Continuation of application No. 13/830,136, filed on Mar. 14, 2013.

(60) Provisional application No. 61/640,781, filed on May 1, 2012.

(51) Int. Cl.
| *A61B 3/14* | (2006.01) |
| *A61B 3/00* | (2006.01) |
| *A61B 3/10* | (2006.01) |
| *A61B 3/02* | (2006.01) |
| *A61B 3/113* | (2006.01) |

(52) U.S. Cl.
CPC ............... *A61B 3/113* (2013.01); *A61B 3/0025* (2013.01); *A61B 3/0041* (2013.01)
USPC ........... 351/209; 351/200; 351/203; 351/205; 351/210; 351/221; 351/223

(58) Field of Classification Search
USPC ......... 351/209, 200–201, 203, 205, 210–211, 351/246, 222, 237, 223, 239
See application file for complete search history.

(56) References Cited

U.S. PATENT DOCUMENTS

| 8,513,055 B2 | 8/2013 | Reichow et al. |
| 8,529,262 B2 | 9/2013 | Stanley |
| 8,553,936 B2 | 10/2013 | Fogt |
| 2003/0211449 A1 | 11/2003 | Seiller et al. |
| 2007/0057842 A1 | 3/2007 | Coleman et al. |
| 2008/0309616 A1 | 12/2008 | Massengill |
| 2010/0177278 A1 | 7/2010 | Reichow et al. |
| 2011/0007275 A1 | 1/2011 | Yoo et al. |
| 2011/0279666 A1 | 11/2011 | Strömbom et al. |
| 2012/0294478 A1 | 11/2012 | Publicover et al. |
| 2014/0184550 A1 | 7/2014 | Hennessey et al. |

FOREIGN PATENT DOCUMENTS

| CA | 2209886 A1 | 1/1998 |
| DE | 196 24 135 A1 | 12/1997 |
| EP | 1 300 108 A1 | 4/2003 |
| WO | WO 01/74236 A1 | 10/2011 |

OTHER PUBLICATIONS

International Search Report and Written Opinion for PCT/US2013/038887 mailed Aug. 7, 2013 (9 pages).

*Primary Examiner* — Dawayne A Pinkney
(74) *Attorney, Agent, or Firm* — Bookoff McAndrews, PLLC

(57) ABSTRACT

Systems and methods are disclosed for evaluating human eye tracking. One method includes receiving data representing the location of and/or information tracked by an individual's eye or eyes before, during, or after the individual performs a task; identifying a temporal phase or a biomechanical phase of the task performed by the individual; identifying a visual cue in the identified temporal phase or biomechanical phase; and scoring the tracking of the individual's eye or eyes by comparing the data to the visual cue.

20 Claims, 12 Drawing Sheets

SYSTEMS AND METHODS FOR EVALUATING HUMAN EYE TRACKING

RELATED APPLICATION

This application claims the benefit of priority to U.S. application Ser. No. 13/830,136 filed Mar. 14, 2013, which claims the benefit of priority to U.S. Provisional Patent Application No. 61/640,781, which was filed on May 1, 2012, the entireties of which are incorporated herein by reference.

TECHNICAL FIELD

Various embodiments of the present disclosure relate generally to evaluating human eye movement. More specifically, exemplary embodiments of the present disclosure relate to systems and methods for tracking and scoring human eye movement, and to recommending tasks to improve motor and cognitive skills based on eye movement.

BACKGROUND

Professionals or experts who have a vast amount of experience with a motor and/or cognitive task are often admired for their physical qualities, such as strength, speed, and coordination. They are also admired for qualities that are less evident, such as being in the right place at the right time and for the ability to strategically "out smart" a difficult situation. These more subtle qualities may be indicative of a proficiency in cognitive understanding. Research has found that professionals or experts who have a vast amount of experience in a variety of different tasks have efficient and effective cognitive processing, as compared to less skilled individuals.

An indication of cognition is evidenced by where one looks in order to detect and utilize the most important information in an environment. Eye movements reflect where a person is looking and searching in the environment, which may be referred to as "visual search." Visual search patterns are typically not random but instead may be learned responses to environmental stimuli. Research has found that optimal visual search and selection patterns develop through experience and are different for experts and novices. One example includes soccer experts, who look at a kicker's hip (a pre-contact cue) to accurately determine and quickly react to the direction where the ball is going. Novices, comparatively, tend to focus on the ball, causing a longer time to make a decision and to initiate a movement.

Typically, experts show systematic visual search patterns from one viewing to the next and repeatedly look at the same locations to detect information. Still further, research has found that experts selectively and consistently attend to the most salient aspects when watching the task in which they are proficient. The visual search patterns of experts enable them to produce significantly higher numbers of correct responses regarding expected outcomes. As another example, expert tennis players are often able to determine the type of spin and direction of the ball from understanding visual components that are present within the environment even before the ball is contacted. Expert tennis players are able to do this better than those with less experience. Another example includes expert drivers who are able to search within their environment and "read" the road in order to avoid potential hazards. Expert drivers have more efficient cognitive and visual search strategies, enabling them to reduce the "cognitive load" and in turn "freeing up" valuable processing space should an unexpected event occur on the road, such as a child running across the road after a ball. Experts also report significantly higher levels of confidence in their responses than do novices.

Decision making capabilities can be affected by visual search patterns. One example includes law enforcement officers responding to a domestic violence situation. As the situation increases in tension, experienced police officers look at the hands of the violent person, whereas inexperienced officers look at the face of the violent person, and were late in seeing a gun being drawn, as well as significantly less likely to make the correct decision to shoot or not-shoot. The visual search patterns of experts also may enable them to initiate a movement faster than novices, such as pressing a brake in a car, running toward a location to intercept a ball, or firing a weapon.

The quality of motor responses also has been found to differ when less effective visual search patterns are used between people of similar skill level. For example, statistics have tested the quality (depth and accuracy) of service return between college level tennis players while measuring their visual search patterns on the tennis court. Results revealed that the players with less salient visual search behaviors were judged lowest in quality of service return. Hence, the cognitive understanding that experts have when watching a skill is evidenced via superior visual search strategies that provide them with an ability to anticipate more accurately than those with less experience and less effective visual search. This capacity also has been shown to relate to faster motor responses of a higher quality performance.

Effective visual search may be particularly important when watching an event unfold rather than reacting to the consequence of an event. For instance, looking for the baseball from a pitcher while standing in the batting position will provide little help in hitting the baseball, especially when the ball is traveling too fast for vision to track the ball. Instead, effective visual search involves looking at biomechanical cues within the motion of the pitch (e.g., arm rotation, grip, release point) in order to effectively read the type and velocity of the pitch.

Furthermore, the eye can track an object with precision and using focal vision only when there is slow relative movement between the observer and the object. The eyes can smoothly move together following the object until visual angular velocities reach 40 to 70 degrees per second. In observing human movement, this translates to surprisingly slow movements, like a person walking (3 mph) slowly past an observer six feet away. Therefore, when a task is occurring very fast, it may not matter if a person has perfect visual acuity and visual strength. What may matter is if they have effective visual search that enables them to pick up early occurrences within biomechanical phases (or pre-cues) that present themselves more slowly and help predict future outcomes, such as velocity, spin, and direction.

Thus, there is a need for systems and methods to evaluate human eye movement. In addition, there is a need for systems and methods to track and score individuals' eye movements, and recommend training tasks for individuals to improve their visual search and other eye movements.

SUMMARY OF THE DISCLOSURE

According to certain embodiments, methods are disclosed for evaluating human eye tracking. One method includes: receiving data representing the location of and/or information tracked by an individual's eye or eyes before, during, or after the individual performs a task; identifying a temporal phase or a biomechanical phase of the task performed by the individual; identifying a visual cue in the identified temporal phase or biomechanical phase; and scoring the tracking of the individual's eye or eyes by comparing the eye location data to the visual cue.

According to certain embodiments, systems are disclosed for evaluating human eye tracking. One system includes a data storage device storing instructions for evaluating human eye tracking; and a processor configured to execute the instructions to perform a method including: receiving data representing the location of and/or information tracked by an individual's eye or eyes before, during, or after the individual performs a task; identifying a temporal phase or a biomechanical phase of the task performed by the individual; identifying a visual cue in the identified temporal phase or biomechanical phase; and scoring the tracking of the individual's eye or eyes by comparing the data to the visual cue.

According to certain embodiments, a computer readable medium is disclosed storing instructions that, when executed by a computer, cause the computer to perform a method of evaluating human eye tracking, the method including receiving data representing the location of and/or information tracked by an individual's eye or eyes before, during, or after the individual performs a task; identifying a temporal phase or a biomechanical phase of the task performed by the individual; identifying a visual cue in the identified temporal phase or biomechanical phase; and scoring the tracking of the individual's eye or eyes by comparing the data to the visual cue.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 8 is a schematic diagram of an exemplary display of evaluations of individuals' eye movements and recommended training tasks for individuals to improve their visual search and other eye movements, according to an exemplary embodiment of the present disclosure;

FIG. 9 is a schematic diagram of an exemplary display of evaluations of individuals' eye movements and recommended training tasks for individuals to improve their visual search and other eye movements, according to an exemplary embodiment of the present disclosure;

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

In view of the background and problems outlined above, systems and methods are disclosed in which motor skills, cognition, and/or kinesiology of a participant may be improved through an iterative process of tracking eye movement, scoring the observed eye movement, reporting or displaying the scoring to the participant, recommending training to the participant based on the scores or observed eye movement, and repeating the process after training has occurred. Certain embodiments of the presently disclosed methods may also include selective modification or combining scores to adjust measurement and target values.

Participants of the present embodiments may include any people desiring to improve their motor skills, cognition, and/or kinesiology, such as any individuals who perform physical activities that require observation and decision making ahead of physical or mental action. These participants can include athletes, pilots, drivers, heavy machine operators, lab equipment technicians, physicians, law enforcement professionals, and/or any other individuals involved in actions that require a cognitive process in order to respond more effectively and efficiently. Alternatively, the participants may be learning or cognitively impaired individuals seeking to improve their mental and physical abilities.

Figure 1:
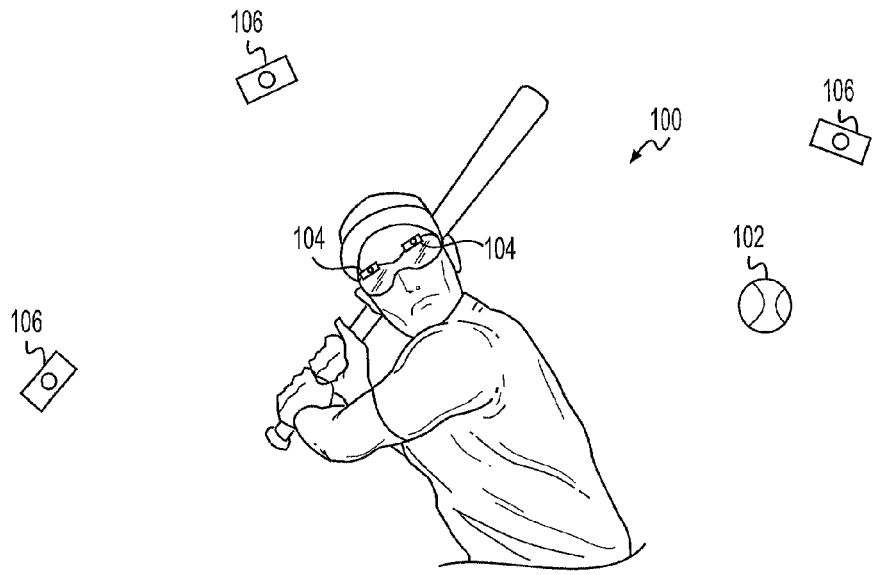
FIG. 1 is a conceptual illustration of an exemplary environment in which the disclosed systems and methods may be used to evaluate individuals' eye movements, and recommend training tasks for individuals to improve their visual search and other eye movements, according to an exemplary embodiment of the present disclosure.

FIG. 1 is a conceptual illustration of an exemplary environment in which the disclosed systems and methods may be used to evaluate individuals' eye movements, and recommend training tasks for individuals to improve their visual search and other eye movements, according to an exemplary embodiment of the present disclosure. Specifically, FIG. 1 depicts an athlete, i.e., a baseball player 100 engaged in a task of observation and decision making ahead of mental and physical action, i.e., hitting a baseball 102. In view of the participants listed above, it should be appreciated that, although FIG. 1 depicts a baseball player for purposes of illustration, the presently disclosed systems and methods are applicable to any individuals engaged in actions that require a cognitive process in order to respond more effectively and efficiently.

FIG. 1 depicts the athlete 100 as wearing an eye tracking device, the device including, for example, a plurality of cameras 104. In addition, FIG. 1 depicts a plurality of remote cameras 106, which may be pointed at the athlete 100 and configured to track and image the athlete's eyes. That is, both wearable cameras 104 and remote cameras 106 may be configured to follow the movement of the athlete's eyes, such as the athlete's irises and/or pupils. The wearable cameras 104 and remote cameras 106 may also be configured to generate video images of the athlete and the athlete's eyes before, during, and after the physical decision making activity, such as striking a target, e.g., baseball 102. Again, it should be appreciated that athlete 100 may alternatively be a machine operator, musician, physician, etc.

In one embodiment, wearable cameras 104 and/or remote cameras 106 may be provided with additional sensors, such as a heat sensing device, a GPS device, a radio frequency ID ("RFID") device, or any other sensors that aid in the detection of human eyes, the location and/or orientation of the human eyes, and/or the location and/or orientation of the wearable cameras 104 and/or remote cameras 106. In one embodiment, wearable cameras 104 and/or remote cameras 106 may include, but are not limited to, webcams, video cameras, remote eye trackers, mobile phones, and/or tablet computers. Wearable cameras 104, in particular, may also or alternatively include or be incorporated into spectacles, visors, helmets, implanted devices, and/or contact lenses. Wearable cameras 104 and/or remote cameras 106 may also include or be provided in communication with physiological monitors, neuroimaging devices, and biomechanical technologies for virtual reality and simulation technologies use with eye data and other scoring or grading. In addition, the methods and systems of the disclosed embodiments may be used with other devices to track eye movements.

Figure 2:
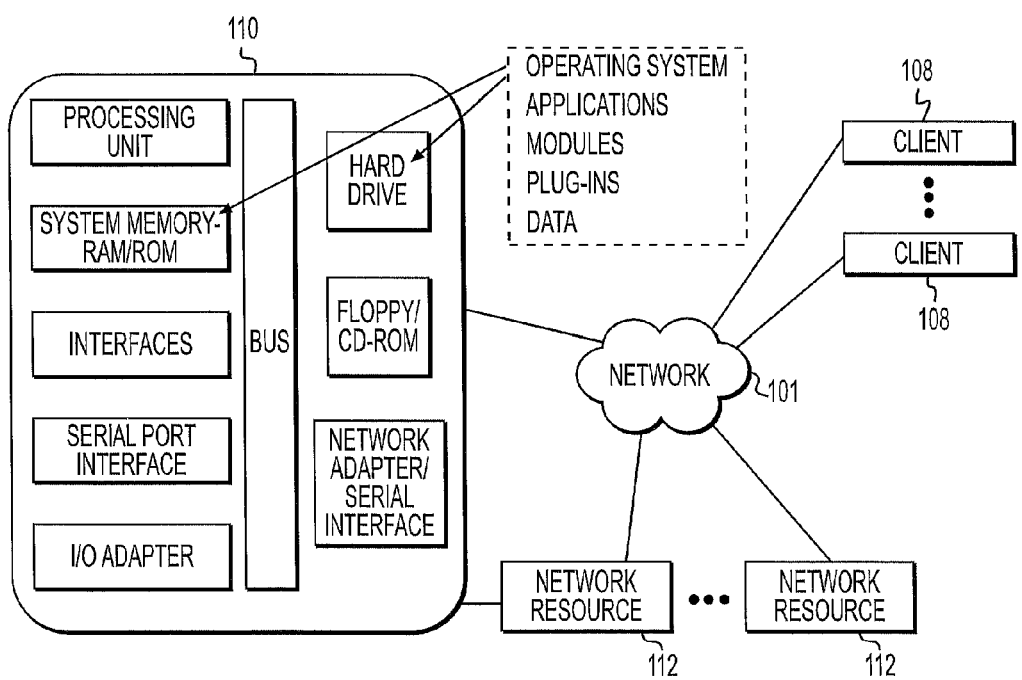
FIG. 2 is a block diagram of exemplary systems for evaluating individuals' eye movements, and recommending training tasks for individuals to improve their visual search and other eye movements, according to an exemplary embodiment of the present disclosure.

FIG. 2 is a block diagram of exemplary systems for evaluating individuals' eye movements, and recommending training tasks for individuals to improve their visual search and other eye movements, according to an exemplary embodiment of the present disclosure. Specifically, FIG. 2 depicts an eye evaluation system 110, a plurality of network resources 112, and a plurality of client devices 108, all provided in communication with an electronic network 101, such as the Internet.

In one embodiment, client devices 108 may be devices owned and/or used by one or more people or organizations affiliated with, or in communication with, an operator of eye evaluation system 110. In one embodiment, client devices 108 may be used by customers or clients of the operator of eye evaluation system 110. For example, people or organizations desiring to have their eyes (or members' or employees' eyes) evaluated may use client devices 108 to send and receive information from eye evaluation system 110. In one embodiment, client devices 108 may send to eye evaluation system 110 one or more of: registration information, biometric information, eye information, activity information, and so on. Client devices 108 may also receive from eye evaluation system 110 one or more of: eye tracking information, eye scoring information, recommended training tasks, reports, and so on. In one embodiment, client devices 108 may be computers or mobile devices through which customers of an eye evaluation entity interact with eye evaluation system 110.

In one embodiment, the devices of clients 108 may include any type of electronic device configured to send and receive data, such as websites and multimedia content, over electronic network 101. For example, each of the devices of clients 108 may include a mobile device, smartphone, personal digital assistant ("PDA"), tablet computer or any other kind of touchscreen-enabled device, a personal computer, a laptop, and/or server disposed in communication with electronic network 101. Each of the devices of clients 108 may have a web browser and/or mobile browser installed for receiving and displaying electronic content received from one or more of web servers affiliated with the eye evaluation system 110. Each of client devices 108 may have an operating system configured to execute a web or mobile browser, and any type of application, such as a mobile application.

Eye evaluation system 110 may include any type or combination of computing systems, such as handheld devices, personal computers, servers, clustered computing machines, and/or cloud computing systems. In one embodiment, eye evaluation system 110 may be an assembly of hardware, including a memory, a central processing unit ("CPU"), and/or optionally a user interface. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The user interface may include any type or combination of input/output devices, such as a display monitor, touchpad, touchscreen, microphone, camera, keyboard, and/or mouse. Eye evaluation system 110 may be configured to send and receive information from network resources 112 and/or clients 108 over the electronic network 101. In one embodiment, eye evaluation system 110 may be in direct local contact with one or more of network resources 112.

In one embodiment, network resources 112 may include any type of device configured to collect and send useful information to eye evaluation system 110 for tracking and scoring eye movement. For example, network resources 112 may include one or more of: wearable cameras 104 and/or remote cameras 106, one or more sensors, such as a heat sensing device, a GPS device, an RFID device, or any other sensors that aid in the detection of human eyes, the location and/or orientation of the human eyes, and/or the location and/or orientation of the wearable cameras 104 and/or remote cameras 106. In one embodiment, network resources 112 may include, but are not limited to webcams, video cameras, remote eye trackers, mobile phones, tablet computers, spectacles, visors, helmets, implanted devices, and/or contact lenses. In one embodiment, one or more of network resources 112 may be configured with network adapters to communicate information to eye evaluation system 110 over network 101. Alternatively, or additionally, one or more of network resources 112 may be configured to transmit and receive information from eye evaluation system 110 directly over a local connection. Network resources 112 may be owned and operated by an operator of one or more of: eye evaluation system 110, client devices 108, or even an outsourced third party, such as an eye tracking specialist.

As will be described in more detail below, eye evaluation system 110 may be configured to receive information, such as eye location and movement information, participant information, etc., either from client devices 108, network resources 112, and/or any other location over the network 101, and process the received information to perform various methods of tracking and scoring eye movement, and recommending training tasks to participants to improve eye movement, consistent with the exemplary methods described below.

Figure 3:
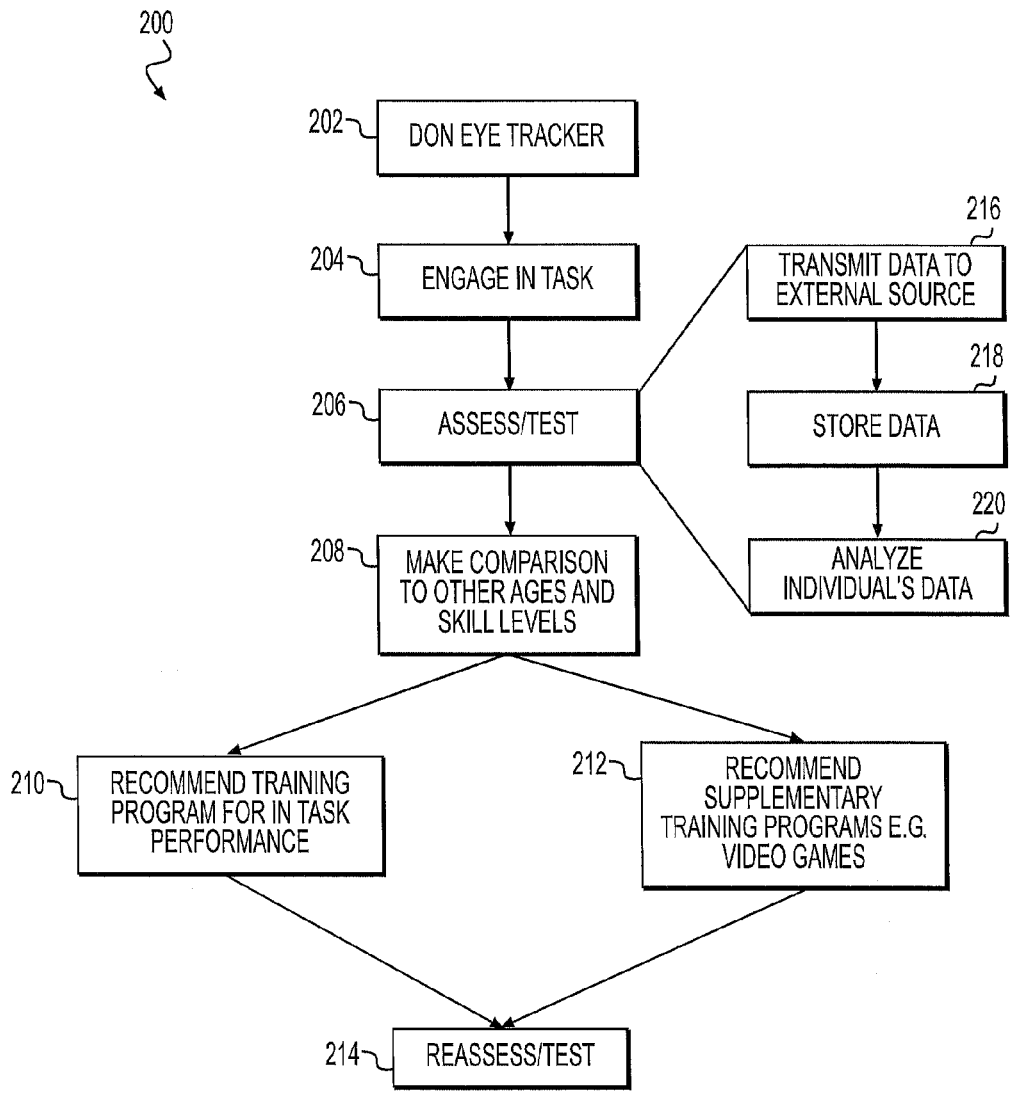
FIG. 3 is a flow diagram of an exemplary method for evaluating individuals' eye movements, and recommending training tasks for individuals to improve their visual search and other eye movements, according to an exemplary embodiment of the present disclosure.

FIG. 3 is a flow diagram of an exemplary method for evaluating individuals' eye movements, and recommending training tasks for individuals to improve their visual search and other eye movements, according to an exemplary embodiment of the present disclosure. Specifically, FIG. 3 depicts a method 200, which may be performed by both an operator of eye evaluation system 110 and a participant, e.g., an individual or entity desiring to improve eye movement.

As shown in FIG. 3, method 200 may include donning an eye tracker (step 202). For example, an individual may don one of wearable cameras 104, whether implemented in a pair of glasses, a visor, a helmet, a pair of contacts, and so on. Alternatively or additionally, the participant may simply position himself or herself in the view of one or more remote cameras 106. Method 200 may then include engaging in a task (step 204). For example, as discussed above, the participant may engage in any task that involves decision making before performing a physical action, such as a sports activity (e.g., swinging a baseball bat, a golf club, a foot at a ball, etc.), landing a plane, turning a corner, loading a pallet, performing a surgical procedure, etc.

Method 200 may then include assessing the participant's eye movement (step 206). In one embodiment, assessing the participant's eye movement may include transmitting data collected from one or more eye trackers to an external source (step 216), storing the data (step 218), and analyzing the participant's data (step 220). For example, data may be obtained from one or more of wearable cameras 104 and remote cameras 106, and transmitted to eye evaluation system 110. In one embodiment, the participant's eye tracking data may be analyzed according to the methods described below with respect to FIGS. 4-6. Specifically, the participant's eye movement data may be analyzed so as to generate one or more scores, including one or more of a "target score," a "cognitive load score," and a "stress indicator score," as will be described in more detail with respect to FIGS. 4-6.

Method 200 may then include making comparisons between the analysis of the participant's eye movement and the eye movement of other participants in the same or different age and skill levels (step 208). In certain embodiments, a target score, cognitive load score, and stress potential indicator score (both ideal scores and actual scores) may be determined based on skill level. In addition, those scores may be compared to ideal visual search levels for a particular skill level for each specific task determined by expert level subjects' visual search patterns. In some embodiments, measuring skill level and/or diagnosing levels of proficiency may occur at various times in the present and future. Measuring skill levels may also include implementing predictive reasoning equations and/or scores.

In one embodiment, method 200 may then include either or both of: recommending training programs for in-task performance (step 210) and recommending supplementary training programs (step 212). In one embodiment, method 200 may include developing and selecting on-field/court drills or on- or off-court games based on the comparisons in order to facilitate learning and improve performance of the participant or team. In one embodiment, recommended training programs for in-task performance (step 210) may include recommending on-field or on-court training drills, whereas recommending supplementary training programs (step 212) may include tasks such as practicing using a video game system or virtual simulator.

In one embodiment, recommending in-task performance training programs in step 210 may include recommending training drills developed based on scientific guidance that provides information on the best way to learn, the process of learning, and/or how people learn to specifically improve perceptual skill training. Training drills may also be developed via in task experiences, for example, from coaches and users. This information may then be used to develop training drills that direct the eyes and/or thoughts to engage in certain behaviors and not others.

In one embodiment, steps 210 and/or 212 may include recommending training drills that are progressive in nature based on a user's (or group of users') eye movement score obtained in step 206. In one embodiment, scores may range from 0-3, 4-7, and 8-10. If a user scores from 0-3, the training drill may be broader in nature with an emphasis on correcting the general characteristics of the eyes and thoughts. A score of 4-7 may generate a training drill that is more specific, for example, including informing the user to look at a specific location and specific movements in time. Finally, a score of 8-10 may generate a drill that is highly specific and sensitive, for example, including looking within a certain degree of visual angle with specific on-set and off-set times while having to interpret what is being seen.

In one embodiment, the process for generating scores and training drills may include, the participant engaging in the task (step 204), transmitting data to the eye score servers (step 216), scoring the task using an eye score scoring tool (step 220) to generate a specific score, e.g., based on a specific moment in time and/or a specific location and/or eye behavior; and linking scores for each moment in time to a specific database code that pulls, e.g., a training recommendation video into a report for the user to access (steps 210, 212).

Method 200 may then include reassessing (step 214), such as by repeating steps 216-220. In one embodiment, eye evaluation system 110 may identify and define an overall visual search strategy recommended for the participant and the activity being performed and intended to be improved, e.g. reducing distractions and information intake or improved decision making. In one embodiment, eye evaluation system 110 may provide generic components of effective visual search for the participant and defined activity, e.g. level gaze, like an airplane landing, stable gaze, like a tripod, in some cases also considering cognitive load of participant and related activity.

Figure 4:
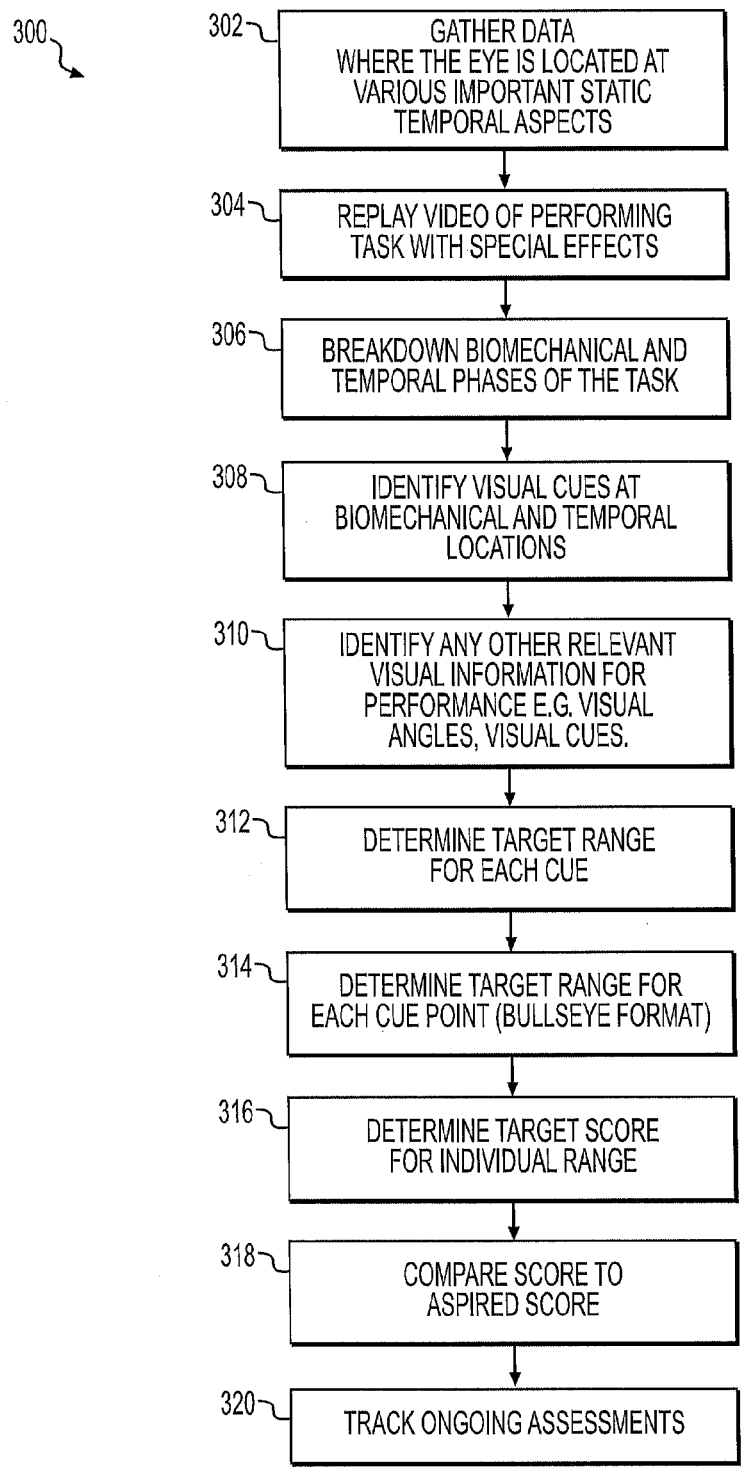
FIG. 4 is a flow diagram of another exemplary method for evaluating individuals' eye movements, according to an exemplary embodiment of the present disclosure.

FIG. 4 is a flow diagram of another exemplary method for evaluating and scoring individuals' eye movements, according to an exemplary embodiment of the present disclosure. Specifically, FIG. 4 depicts another method 300 for gathering eye movement data, analyzing eye movement data, and scoring eye movements. In certain embodiments, one or more scores determined according to method 300 may be referred to as a "target score."

In one embodiment, method 300 may include gathering data on where an eye is located at various temporal aspects (step 302). For example, eye movements may be collected from a variety of eye tracking or similar eye location data collection devices, such as the wearable or remote cameras 104, 106 (FIG. 1) or network resources 112 (FIG. 2).

Method 300 may also include replaying video of performing a task along with special effects (step 304). For example, special effects may include highlighting, enlarging, reducing, blocking, slowing, speeding up video for assessment and/or training purposes. Of course, method 300 may use any other techniques to enhance or replay video of a task in order to improve analysis and understanding of motion or positions of body parts, cues, and/or eye positions in a video.

Method 300 may also include breaking down biomechanical and temporal phases of the performed task (step 306). In one embodiment, a biomechanical phase may be an interval of bodily movement and a temporal phase may be a time interval. For example, eye evaluation system 110 may identify and define specific biomechanical phases of movement to be improved by evaluating the eye movement of a participant and the subsequent decision making carried out by the participant. Within a specific skill, various temporal phases may be identified based on biomechanical, social interaction, and various other important task phases and visual search scientific research. For example, for the task of hitting a baseball, temporal or biomechanical phases may be broken down into a pre-wind-up phase, a wind-up phase, a pitch phase, and a post-release phase. For the task of guarding a soccer penalty kick, the temporal or biomechanical phases may be broken down into the standby phase, the running up phase, the windup phase, the kick phase, and the post-kick phase. Method 300 may include breaking down phases by both timing, and by motions or combinations of motions by the participant or related individuals.

Method 300 may also include identifying visual cues at biomechanical and temporal locations (step 308). A visual cue may be a specific visual location at a point in time during a task where a person may stabilize their vision in order to prepare for an upcoming event. For example, a cue may be defined wherein a goalie should be looking at a kicker's hip, or a cue may be defined wherein a baseball player should be looking at a pitcher's shoulder. Thus, in one embodiment, a cue may be a location on another person's body, a location on a piece of equipment, a location on a vehicle, a location on a surgical instrument, a location on a playing field, a location on a ball or sports object, and so on. In one embodiment, eye evaluation system 110 may identify and define appropriate cues at each biomechanical phase of the participant activity being monitored. For example, visual cues or ideal visual search locations may be determined based on scientific research, libraries of past data, or any other historical research. Moreover, it will be appreciated that certain cues may move with time, and so a location where the participant should be looking may also move with the cue.

Method 300 may also include identifying other relevant visual information for performance (step 310). For example, the method may involve identifying visual angles and/or visual cues. In one embodiment, visual angles may be measured by entering the size and viewing distance from the stimulus. Visual angle may affect a person's depth perception, which may be important for the person to exhibit temporal accuracy over distance. For example, a parallax error may occur when the eyes do not move together to track an object over a distance. Thus, visual cues may be tracked over various distances and therefore may be relevant visual information for performance.

Method 300 may also include determining a target range for each cue (step 312). For example, target ranges may define a distance away from a cue within which the individual should ideally look. In one embodiment, target ranges for ideal eye locations may be collected from a variety of eye tracking or similar eye location data collection devices at various temporal phases with a static image. In some embodiments, a target range may be relatively static (e.g., look within 50 mm of the center of the goalpost), whereas in other embodiments, a target range may expand or narrow with time. In one embodiment, various ranges of temporal phases may be used to score a level of proficiency in the specific skill at the specific temporal phase. For each important temporal phase, various target ranges may be created to score individuals based on skill level, i.e. beginner through elite levels. For example, a target range for an expert may be narrower than a target range for a beginner.

Method 300 may also include determining a target range for each cue point (step 314). Specifically, in addition to determining a target range for a cue generally, such as, looking within 25 mm of the center of a baseball, a target range may be generated for each cue, at each point in time within a temporal phase of interest. In other words, as a baseball travels from a pitcher to a hitter, the cue itself is moving and the range of coordinates defining the target range may also move. Thus, a target range for each cue point may define a plurality of target ranges that change over time based on the movement of a cue.

Method 300 may then involve calculating a target score based on a comparison of where a participant looked to the individual's target range, for one or more cues in one or more temporal phases of interest (step 316). Specifically, method 300 may generate a score for each important temporal phase that coincides with the target range previously determined for the specific skill level of the individual. An overall score may then be generated by combining the score of each important temporal phase. In one embodiment, the target score, whether calculated for each temporal phase, each cue, or an overall score, may be calculated according to the embodiments of FIG. 5 and/or FIG. 6, as described below.

Method 300 may also include comparing the calculated target score to an aspired or ideal score (step 318). For example, based on the scores and/or all results of each important temporal phase and/or the combined score, the individual may receive a specific report and/or images of each temporal phase with their specific eye locations, and comparisons to ideal scores and/or eye locations. This report may compare and explain the score and/or training recommendations to help achieve the sought after eye location at each important temporal phase. An explanation of the importance of eye location within the sought after target range may also be provided in the report. Based on this report, various in-task and related-to-task training tools may be recommended to the individual to be applied, including training games, video games, training drills and/or other training programs, as described above.

Embodiments of method 300 may therefore include conducting data analysis and/or comparisons by storing a participant's visual search patterns, plotting a visual search pattern over time, generating algorithms and reference points to provide feedback to the participant on their visual search patterns compared to others, and reporting on proficiencies and gaps in visual search performance. Embodiments may also include autonomously tracking and gathering eye movements of a participant or a team, generating a target score, and comparing the gathered data and target score against a benchmark. This comparison may include identifying where a participant looks based on his or her skill level, and identifying the emotional state of the participant and whether or not this emotional state is compromised.

Method 300 may also include tracking ongoing assessments (step 320). In other words, method 300 may then include gathering further data, determining new target ranges, and calculating new scores, based on later rounds of performing the task, for example, to determine the effectiveness of training recommended, such as in steps 210 and 212 of FIG. 3. Reassessment and/or reevaluation may include additional data gathering for the individual to compare with baseline assessment and/or evaluation results, including the score for each important temporal phase and/or the combined score for each important temporal phase. These eye locations at each important temporal phase may be compared to the previously determined target ranges from the individual's score and/or the score which coincides with the target range previously determined for the specific skill level or the individual. Based on a participant's scores for each important temporal phase and/or the combined score, the individual may receive an updated specific report and/or images of each temporal phase with their specific eye locations. This report may compare and explain the score, and/or all results, from evaluation and/or assessment to reevaluation and/or reassessment. All information, including but not limited to eye movement data, target ranges, individual reports, recommendations, training games, video games, training drills and/or other training programs may be accessed in electronic form including but not limited to a password protected website, mobile application, etc.

Figure 5:
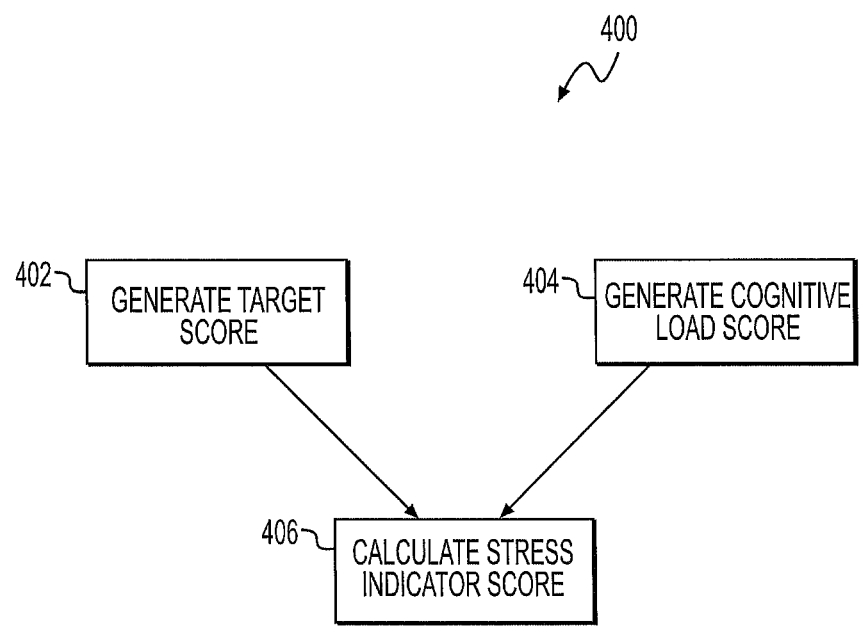
FIG. 5 is a flow diagram of another exemplary method for evaluating individuals' eye movements, according to an exemplary embodiment of the present disclosure.

FIG. 5 is a flow diagram of another exemplary method 400 for evaluating individuals' eye movements based in part on the "target score" calculated as described in FIG. 4, according to another exemplary embodiment of the present disclosure. Specifically, FIG. 5 depicts a method including generating a target score of a participant (step 402), such as by performing one or more steps of method 300 of FIG. 4. Method 400 may also include generating a cognitive load store (step 404), as will be described in more detail below. Finally, method 400 may include calculating a stress indicator score (step 406), based on one or both of the generated target score (step 402) and generated cognitive load score (step 404). One embodiment may include generating a target score, generating a cognitive load score, and then calculating a stress indicator score based on the generated target score and the generated cognitive load score. In one embodiment, the stress indicator score may be calculated as the sum of the generated target score and the generated cognitive load score.

| Score/Grade | Test 1 | Test 2 | Test 3 |
| --- | --- | --- | --- |
| Target ™ Score | 1.8 | 6.5 | 9.0 |
| Cognitive Load ™ Score | +32 | +12 | +6 |
| Stress Potential Indicator ™ Grade | HIGH | MEDIUM | LOW |

Step 404: Exemplary Cognitive Load Score Generation

In one embodiment, a cognitive load score may be calculated in step 404 based on the number of eye movement shifts divided by beginning-and-ending-time-points where various target ranges of cognitive load results may be used to score cognitive load. As described above with respect to calculation of the target score, eye evaluation system 110 may calculate the cognitive load score based on information received from any of cameras 104, 106, network resources 112, or any other external sources.

As used herein, "cognitive load" may refer to the load or "effort" related to the executive control of a participant's working memory (WM). Eye tracking can be used as a tool to represent "cognitive load" as the eyes are used to process the external environment and eye movements can be used to explore the "load" of external and internal processing of brain activity. For each specific task, various beginning and ending times may be defined, and an ideal number of shifts in eye movements may be identified. Shifts in eye movements may include but are not limited to fixations, saccades, and pursuit tracking. Eye movements may be collected from a variety of eye tracking or similar eye location data collection devices. Within a specific skill, cognitive load may be determined based on the number of eye movement shifts divided by beginning-and-ending-time-points during the specific task. For each specific task, an ideal number of shifts in eye movements may be determined based on skill level. Various target ranges of cognitive load results may be used to score the level of cognitive load for the specific skill. For each skill, various target ranges may be created to score individuals based on cognitive load processing level, i.e. beginner through elite levels. In one embodiment, a cognitive load score may be defined by the following formula:

$$\text{cognitive load score} = \frac{\text{eye movement characteristic}}{\text{time}} \times \frac{100}{1}$$

Data gathering for an individual baseline assessment and/or evaluation may include collecting beginning and ending times, and the number of shifts in eye movements for the individual. These beginning and ending times and the number of shifts in eye movements may be compared to the previously determined target ranges. The individual may receive a score, which coincides with the target range previously determined for the specific skill level of the individual. An overall score may be used by combining the score of each beginning and ending time. Based on the scores and/or all results of each beginning and ending time and/or the combined score, the individual may receive a specific report and/or images and/or video of each beginning-and-ending-time-point with their specific shifts in eye movements. This report may compare and explain the score and/or training recommendations to help achieve the sought after reduction in eye movement shifts at each beginning-and-ending-time-point. An explanation of the importance of eye movement shifting within the sought after target range may be provided in the report. Based on this report, various in-task and related-to-task training tools may be recommended to the individual to be applied, including training games, video games, training drills and/or other training programs.

Step 406: Exemplary Stress Indicator Score Generation

As described above, in one embodiment, the stress potential indicator score may be a combination of one or more of the target range scores and one or more of the cognitive load scores. In one embodiment, eye evaluation system 110 may calculate the stress indicator score based on prior calculations of target range scores and stress indicator scores, and/or based on information received from external sources. In one embodiment, for each specific task, an ideal stress indicator score may be determined based on skill level. Various target ranges of stress indicator results may be used to score a level of potential for the specific skill. For each skill, various target ranges may be created to score individuals based on stress potential indicator levels, i.e. beginner through elite levels. In one embodiment, the stress indicator score may be calculated as the sum of the target score and the cognitive load score. This may therefore include determining where the individual's stress indicator score lies within a range indicating level of stress and ultimately a representation back to the user of the level of stress currently assessed. This representation may or may not include a depiction of a thermometer, e.g., from 1 to 100 degrees, or some other visual representation of the user's stress indicator score, either compared to others and/or to a metric indicating the maximum through minimum levels of stress possible.

Based on the scores and/or all results of one or more of the target range scores, and added with one or more of the cognitive load scores, the individual may receive a specific report and/or images of one or more of their specific target range scores and added with one or more of the cognitive load scores. This report may compare and explain the score and/or training recommendations to help achieve the sought after reduction in stress indicator score at each one or more of the target range scores and added with one or more of the cognitive load scores. An explanation of the importance of stress potential indicator score within the sought after target range may be provided in the report. Based on this report, various in-task and related-to-task training tools may be recommended to the individual to be applied, including training games, video games, training drills and/or other training programs.

Figure 6:
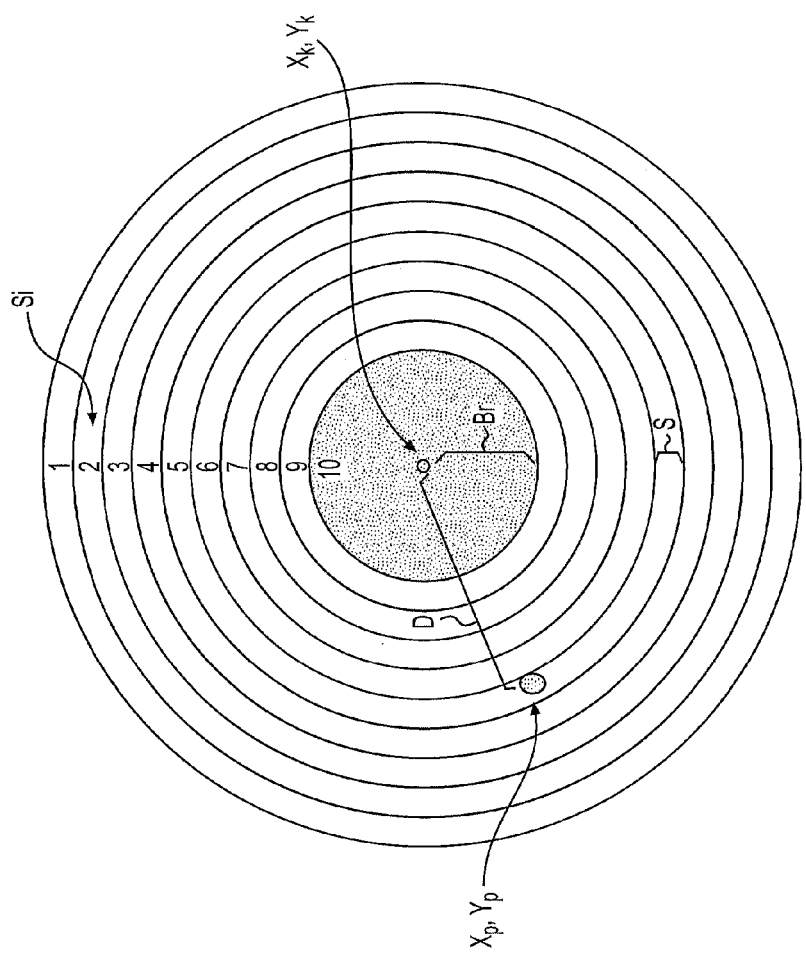
FIG. 6 is a schematic diagram of a framework for evaluating and scoring individuals' eye movements, according to an exemplary embodiment of the present disclosure.

FIG. 6 depicts a schematic diagram of one exemplary framework for calculating an eye tracking score of an individual, by comparison with a target location where an individual ideally should have looked. As shown in FIG. 6, in one embodiment, a framework for calculating a target eye score may be based on a bull's-eye arrangement and related variables that may be used in calculating an exemplary eye tracking score. Specifically, FIG. 6 depicts a bull's-eye arrangement having a bull's-eye defined by point $X_k, Y_k$, which may be the coordinates for the "key value" that represents the center of the bull's-eye, representing a cue point, or where a participant ideally should have looked. The bull's-eye arrangement of FIG. 6 also depicts an exemplary point $X_p, Y_p$, which may be the coordinates for the "point of regard" ("POR"), i.e., where the participant was actually looking.

In one embodiment, calculation of a target score consistent with the bull's-eye of FIG. 6 may include one or more of the following constants:

Br—A constant indicating the bull's-eye radius (e.g. 25 mm);

Sc—A constant indicating the scale of a segment increment, which may specify what portion of the bull's-eye radius (Br) is used as a segment increment (S), where standard scales may include 1/5, 2/5, 1/3, 1/4, 1/2;

S—A "segment increment," or amount that each segment ring is increased by over the bull's-eye radius (Br), where each ring is incremented by the same segment increment amount based on the scale (Sc), such that S=Br*Sc;

Si—A segment index, which may be the index value of the segment ring that relates to the target score for being within that ring; and D—A distance between the bull's-eye center and $X_p, Y_p$ (i.e., the POR), where:

$$D = \sqrt{(X_k - X_p)^2 + (Y_k - Y_p)^2}$$

Based on the above constants and distance formula, the distance of each ring of the circle from the bull's-eye center $(X_k, Y_k)$ may be calculated by multiplying the bull's-eye radius (Br) by the scale (Sc) to determine the scale increment (S). For example, where Br=25 mm and Sc=1/5 or 0.2, then S=5 mm. The segment increment (S) may then be added to the bull's-eye radius (Br) for each segment index (Si) to get the distance for each ring. The table below illustrates sample calculations given a bull's-eye radius of 25 mm.

| Segment Index (Si) | mm from Bull's-eye Center | Calculation |
| --- | --- | --- |
| 10 | 25 | 25 |
| 9 | 30 | 25 + 5 |
| 8 | 35 | 25 + (5 * 2) |
| 7 | 40 | 25 + (5 * 3) |
| 6 | 45 | 25 + (5 * 4) |
| 5 | 50 | 25 + (5 * 5) |
| 4 | 55 | 25 + (5 * 6) |
| 3 | 60 | 25 + (5 * 7) |
| 2 | 65 | 25 + (5 * 8) |
| 1 | 70 | 25 + (5 * 9) |

Thus, the distance for each segment ring may be represented by the following formula, using the segment index (Si) as a multiplier for the segment increment (S), as follows:

Segment Distance$_{Si}$=Br+((Br*Sc)*(10−Si))

Therefore, when the distance (D) where the participant was looking is exactly equal to one of the segment distances, then the segment index (Si) may be defined as the participant's "target score." In other words, the segment distance$_{(si)}$ formula above may be solved for Si, which provides a formula to solve for the target score where D=Segment Distance$_{(si)}$, such that:

D=Br+((Br*Sc)*(10−Si))

and solving for Si defines the following formula:

$$Si = 10 - \left(\frac{D - Br}{Br * Sc}\right)$$

Thus, when Si is defined as the "target score"—also referred to as a proprietary "RightEye Score," such a score may be defined by the following formula:

$$RightEye\ Score = 10 - \left(\frac{D - Br}{Br * Sc}\right)$$

If it is desired to expand the formula from the X,Y coordinates of the bull's-eye key center and point of regard, then the target score or "RightEye Score" may be defined by the following formula:

$$RightEye\ Score = 10 - \left(\frac{\left(\sqrt{(X_k - X_p)^2 + (Y_k - Y_p)^2}\right) - Br}{Br * Sc}\right)$$

As a result, a target score value for any distance or X,Y coordinates may be calculated, resulting in values from 0 to 10. As described above, a higher target score indicates that the participant was looking close to the cue point, where as a lower target score may indicate that the participant was looking relatively farther away from the cue point. As described above, in one embodiment, scores may be grouped from 0-3, 4-7, and 8-10. If a user scores from 0-3, a recommended training drill may be broader in nature with an emphasis on correcting the general characteristics of the eyes and thoughts; a score of 4-7 may generate a training drill that is more specific, for example, including informing the user to look at a specific location and specific movements in time; and a score of 8-10 may generate a drill that is highly specific and sensitive, such as looking within a certain degree of visual angle with specific on-set and off-set times while having to interpret what is being seen.

In one embodiment, this exemplary technique for generating the target score may adjust the scale with a smaller or larger bull's-eye radius based on one or more various factors, such as the distance from the subject to target, the participant's skill level, and so on. The table below depicts exemplary target score calculations given certain point of regard and bull's-eye coordinates, and a bull's-eye radius of 25 mm.

| Bull's-eye Radius = 25 Trial/Rep Number | POR X | POR Y | Key X | Key Y | Distance | Target Score Calculation 1/5 Scale | Target Score Adjusted |
|---|---|---|---|---|---|---|---|
| 1 | 200 | 300 | 200 | 300 | 0.0 | 15.0 | 10 |
| 2 | 220 | 330 | 200 | 300 | 36.1 | 7.8 | 7 |
| 3 | 190 | 320 | 200 | 300 | 22.4 | 10.5 | 10 |
| 4 | 180 | 290 | 200 | 300 | 22.4 | 10.5 | 10 |
| 5 | 150 | 310 | 200 | 300 | 51.0 | 4.8 | 4 |
| 6 | 260 | 400 | 200 | 300 | 116.6 | -8.3 | 0 |

Additional Exemplary Evaluation Metrics (i.e., Scoring)

The above-described methods of FIGS. 3-5 describe a plurality of different scores that may be used to evaluate eye movement, including the target score, cognitive load score, and stress indicator score. Moreover, the present disclosure describes the bull's-eye framework of FIG. 6 as one exemplary technique for generating a target score. However, it should be appreciated that any number or type of additional scores may be used to evaluate eye movement. The following is a list of additional scores or factors that may be evaluated, calculated, and/or scored, and incorporated into one or more of the target score, cognitive load score, and stress indicator score. Any of the following scores may be generated by eye evaluation system 110 and displayed to a client device 108 in addition to the target score, cognitive load score, and/or stress indicator score. Alternatively, any of the following scores may be calculated and incorporated as an element or component of one or more of the target score, cognitive load score, and stress indicator score.

Visual Relax Score:

In one embodiment, a visual relax score may evaluate a visual search pattern (including fixations, saccades, pursuit tracking and any other eye movement) that is seemingly random and occurs after the completion of one task and before a visual anchor of the next task. The visual relax period may be a low concentration time designed to help the individual relax and restore brain processes between tasks. For example, after a closed skill like hitting a baseball or putting in golf, the user may look at a location, such as the outfield or the hole, to reset and rethink next steps. This may be recommended with some regularity and consistency from one trial to the next. The visual relax score may be marked as present or absent, and a time factor may or may not be associated with the score. In one embodiment, a formula for a visual relax score may or may not be a binary "present" or "not present" recording, and/or a reporting of looking at a specific location, with or without a time metric, to include one or more eye movement characteristics.

Anchor Cue Score:

In one embodiment, an anchor cue score may evaluate a fixation or tracking gaze that is presented on a specific location or object, e.g., within 3 degrees of visual angle for a minimum of 100 milliseconds occurring after the visual relax and before the visual calibration. The anchor cue may be but need not necessarily be close in visual range to the participant (e.g., within 6 feet, depending on the task). The anchor cue may be designed to bring the participant's mental and visual focus back to the task at hand after a time of relaxation (i.e., the visual relax). The anchor cue score may be measured by identification of the cue and may or may not be within a close range of the subject performing the task. In one embodiment, the formula for identifying the anchor cue may or may not include a distance metric, a length of time, and/or specific eye movement characteristics. Examples may include a bat or diamond-like shaped objected (e.g., home plate) for a baseball hitter, a racquet for a tennis player, or the ground in front of a subject for a soccer goal keeper.

Quiet Eye Score:

In one embodiment, a quiet eye score may be a fixation or tracking gaze that may be presented on a specific location or object in the visual motor workspace within, for example, 3 degrees of visual angle for a minimum of 100 milliseconds. For example, a quiet eye may be a fixation on the rim of a basketball hoop prior to making a free throw. The onset of the quiet eye may occur prior to the final movement in the task; the quiet-eye offset may occur when the gaze moves off the location by more than, for example, 3 degrees of the visual angle for a minimum of 100 milliseconds. The quiet eye may be a perception-action variable, in that its onset may be dictated by the onset of a specific movement in the task.

Visual Angle Score:

In one embodiment, a visual angle score may evaluate a degree of horizontal variation from center to left and/or right (x and y coordinates) measured relative to visual object(s) and scene camera angles. One example of a visual angle score may include the angle at which a batter looks at the pitcher. A visual angle score may be represented as a left to right and/or positive to negative range of degrees between 0-360. In one embodiment, a visual angle score may include the distance the subject is from the target, and/or the height and width of the target. The visual angle score may be a metric that influences a vantage point score, described below. In one embodiment, a visual angle score may be calculated according to the formula:

$$\tan V = \frac{S}{D}.$$

for visual angles smaller than 10 degrees; and $$V = 2\arctan\left(\frac{S}{2D}\right),$$

for visual angles greater than 10 degrees.

Vantage Point Score:

In one embodiment, a vantage point score may include the visual angle score as well as the distance and/or velocity an object may be from the subject. The vantage point score may reflect a principle that vision will be most accurate in observing motion at right angles to the line of sight. In one embodiment, the vantage point score may provide a metric indicating the difficulty in the vantage point in order to provide feedback that includes but is not limited to head position, body position, and/or eye position. For example, a vantage point score may show a 20% reduction in optimal visual qualities, measured by the vantage point score due to, e.g., a tennis player looking over their shoulder in a closed stance for the backhand groundstroke instead of positioning their body in an open stance.

Viewing Time Potential Score:

In one embodiment, a viewing time potential score may compare the subject's vantage point score against an ideal vantage point score in order to determine the missing potential in terms of, e.g., angles, velocity, and distance. These metrics may be calculated to determine the potential increase in viewing time of the task. Feedback may be provided to the subject from the viewing time potential score to indicate if vantage point and appropriate body movement can be used to increase viewing time in order to improve performance. One example may include a tennis player's reduction in the viewing time potential of a ball due to a closed stance on a backhand groundstroke. For example, a possible viewing time on a ball may be 2 seconds, whereas the user's actual viewing time may be 1.5 seconds. The viewing time potential score may or may not be represented as a percentage loss, such as a 25% loss of potential.

Visual Calibration Score:

In one embodiment, a visual calibration score may evaluate a scan path that occurs between two objects (measured at, for example, 3 degrees of visual angle for a minimum of 100 milliseconds) at a minimum of one time prior to a task beginning. One example of visual calibration in baseball may include looking at the plate and then to the pitcher, which could occur once or several times in succession without the scan path deviating to another object. The visual calibration score may therefore reflect a participant's compliance with a recommended or target series of calibration tasks.

Visual Lock Score:

In one embodiment, a visual lock score may evaluate a fixation or tracking gaze that may be located on a specific location or object within, for example, 3 degrees of visual angle for a minimum of 100 milliseconds. The onset of the visual lock may occur either after a visual calibration or after a visual relax. The visual lock score may be rated by location applicability for the task. For example, prior to a fast motion, e.g. a soccer penalty kick, the subject should have a visual lock on the opponent's center mass in order to begin with the most effective location for seeing the upcoming event or task. Therefore, in this case, center mass would be the bull's-eye, and if the subject is looking at the center mass after a visual calibration or after a visual relax, then the subject may receive the highest score. The visual lock score may drop as the subject looks away from the center of mass. It should be appreciated that, while the quiet eye score may measure a fixation in any location, the visual lock score may take into account the appropriateness of the location and score this location based on the upcoming task.

Pursuit Tracking Score:

In one embodiment, a pursuit tracking score may evaluate a participant's ability to follow an object, such as a ball, over time and distance. The pursuit tracking score may be a percentage of time tracking an object from one defined location to another within a certain range of visual accuracy around the object. The pursuit tracking score may be given over distance and/or time traveled and represented as a percentage score and/or frame-by-frame score.

Pursuit Tracking Skill Comparison Score:

In one embodiment, a pursuit tracking comparison score may evaluate a percentage of time of tracking an object from one defined location to another within a range of visual angle. The pursuit tracking score may be given over distance and/or time traveled, and represented as a percentage score. The percentage score may then be compared to benchmark scores from other skill levels where a further score may be given to the subject that represents their comparative skill level and/or where they fall within a range of scores.

Focal Tracking Ability Score:

In one embodiment, a focal tracking ability score may evaluate when focal vision is no longer physiologically able to track the object due to speed over time and/or visual space (i.e. closer versus further away). A focal tracking ability score may be compared with a participant's loss of visual tracking to determine if an increase in visual tracking time may be physically possible. One example may be the ability to track a baseball and the determination of when a ball pitched at various speeds will be unable to be seen visually at certain distances from the batter. In one embodiment, the focal tracking ability score may be defined by the following formula:

$$\text{focal tracking ability score} = \frac{\text{speed} + \text{distance}}{\text{time}}$$

Visual Routine Score:

In one embodiment, a visual routine score may evaluate the consistency of visual cue location (measured, for example, at 3 degrees of visual angle for a minimum of 100 milliseconds) associated with task locations over time. Similar to a visual calibration score, the visual routine score may be a measure via a scan path over time between two or more objects. The visual routine score may measure the consistency of visual cue locations across the presentation of the same and/or similar skills. For instance, during the presentation of skill 1, the scan path may be cue A to cue B to cue A. In the presentation of skill 2, which is skill 1 repeated, if the scan path remains the same, i.e., cue A to cue B to cue A, then the visual routine score would be high (a desired result assuming the cues are accurate for the task). However, if the visual scan path changes in presentation of skill 2 (e.g. cue A to cue D to cue A) then a lower score may be assigned due to the deviation in scan path from the presentation of skill 1 to skill 2. The visual routine score may or may not be represented as a percentage and/or as a measure on a scale from high to low. Frequency of the routine may or may not be considered as a metric to determine results and/or score. One example of the visual routine score may be a tennis player viewing a server, where the first cue is on the non-dominant hand, the second cue is the ball, and the third cue is the contact point.

Black Hole Score:

In one embodiment, a black hole score may evaluate saccadic suppression. Saccades may include the movement of the eye at a rate of, for example, less than 100 milliseconds at 3 degrees or greater visual angle, which do not track an object over a distance, but instead reposition eyes quickly from one target of focal vision to the next such that the eyes are essentially turning off as they move via a saccade to the next fixation. An example of a saccade may be an ice hockey goal keeper moving his eyes from one player to the next, stopping (fixating) to look at the players, but moving the eyes quickly (with saccades) from one player to the next. A black hole score may be assigned as a percentage of time, over a task in which the eye moves at a rate of, for example, less than 100 milliseconds at 3 degrees or greater visual angle and is not pursuit tracking. One example may be the time the ice hockey goal keeper uses saccades to read the offensive play of the opposing team toward goal.

$$\text{black hole score} = \frac{\text{saccadic eye movement time}}{\text{overall task time}} \times \frac{100}{1}$$

Response Time Score:

In one embodiment, a response time score may evaluate an interval of time involving both reaction time and movement time, i.e., the time from the onset of a stimulus (e.g. gunshot) to the completion of the movement e.g. crossing the start or finish line. Responses may be but are not limited to motoric and/or verbal responses and/or eye movement. Response time may be defined as follows:

response time score=reaction time+movement time

Reaction Time Scores:

In one embodiment, a reaction time score may evaluate the interval of time between the onset of a signal (stimulus and/or visual cue) and the initiation of a response (verbal and/or motor). One example may be a sprinter in track when they hear the gun and then begin to move to respond to the "go" signal. Responses may be but are not limited to motoric and/or verbal responses and/or eye movement. In one embodiment, reaction time may be calculated from a "Go Signal" zero time to initiation of a response, including premotor and motor components, to any number of stimuli/situations.

Simple Reaction Time Score:

In one embodiment, a simple reaction time score may evaluate when a situation requires only one signal and one action (motor, verbal or eye movement) in response. The example of the sprinter reacting to a gun (the go signal) and responding by running (the action) is an example of simple reaction time. This is the simplest form of reaction time. In one embodiment, reaction time may be calculated from a "Go Signal" zero time to initiation of response, including premotor and motor components, to one stimuli/situation.

Discriminate Reaction Time Score:

In one embodiment, a discriminate reaction time score may evaluate where there is more than one signal, but only one response. For example, three objects appear on a screen: a triangle, square and circle. The athlete needs to only respond to the circle and ignore the square and triangle. Reaction times are usually longer in discriminate reaction time situations than simple reaction time, due to an increase in information processing and decision making needed to respond accurately to the situation. The formula for discriminate reaction time may or may not include an error score. In one embodiment, reaction time may be calculated from "Go Signal" zero time to initiation of response, including premotor and motor components, to one stimuli/situation while ignoring others.

Choice Reaction Time Score:

In one embodiment, a choice reaction time score may evaluate where there is more than one signal to which the person must respond and each signal has a specified response. This is may be referred to as the "If this . . . then that" reaction time. For instance, a training drill related to the choice reaction time score may include displaying a circle on a screen, that a participant must look at, until it disappears. If a square appears on the screen, then the participant must avoid looking at it. If a triangle appears on the screen then the participant must follow it with your eyes as it moves left and right, and so on. In one embodiment, a formula for choice reaction time may or may not include an error score. In one embodiment, choice reaction time may be calculated from a "Go Signal" zero time to initiation of a response, including premotor and motor components, to one stimuli/situation with the correct "choice"/response.

Pre-Motor Component Score:

In one embodiment, a pre-motor component score may evaluation time from the initiation of the "Go Signal" to the beginning of a motor component response. This may be measured through either biofeedback and/or psycho-physiological feedback. In one embodiment, a pre-motor component reaction time may be calculated as a reaction time–motor component.

Motor Time Component Score:

In one embodiment, a motor time component score may evaluate time from the initiation of a motor component, measured via either biofeedback and/or psycho-physiological feedback, until the initiation of a response. In one embodiment, a motor component reaction time may be calculated as reaction time minus a pre-motor component time.

Movement Time Score:

In one embodiment, a movement time score may evaluate the interval of time between the initiation of the movement and the completion of the movement, such as, when a sprinter begins to move in response to the gun until when she crosses the start/finish line. Another example may be when the eyes begin to move until they reach their target. In one embodiment, movement time may be calculated based on the time between initiation of the response until termination of the response.

Inhibition Score:

In one embodiment, an inhibition score may evaluate the ability of a participant to not respond to a target, for instance, to not be distracted by the wind blowing flags beside the tennis court or a car moving behind a sports field. The inhibition score may or may not be measured via number of hits/looks.

Target Over/Undershoot Score:

In one embodiment, a target over/undershoot score may evaluate the amount of constant error beyond the target, the signed deviation (+/−) from the target. For example, the score may represent the amount and direction of error and serve as a measure of performance bias. The over/undershoot score may be signed (+/−) and receive a distance metric. For example, 3 centimeters may refer to stopping 3 centimeters short of the desired target. In one embodiment, the target over/undershoot score may be calculated based on a distance from the center of the target to center of the eye movement stopping point, adding a minus for stopping too early and a plus for overshooting Target Miss Score:

In one embodiment, a target miss score may refer to the unsigned deviation (miss) from the target, representing the amount of error. The target miss score may include the absolute error, a measure of the magnitude of an error without regard to direction of the deviation. The target miss score, for example, may be 3 centimeters and refer to the distance the eye stopped from the target, but not the direction of the error (i.e., stopping short or overshooting). In one embodiment, the target miss score may be calculated based on a distance from the center of the target to the center of the eye movement stopping point.

Target Consistency Score:

In one embodiment, a target consistency score may refer to the variable error representing the variability (or conversely, the consistency) of performance. For example, in one embodiment, standard deviation of the users' target over/undershoot (x) may be calculated based on the score (constant error) for the series of trials, i.e., number (n) of attempts, as follows:

$$s = \sqrt{\frac{\Sigma(x - \bar{x})^2}{n - 1}}$$

Target Movement Score:

In one embodiment, a target movement score may evaluate an error involved in continuous skills, such as following a ball (or object), to indicate the amount of error between the performance curve and the criterion performance curve for a specific amount of time during which the performance is sampled. In one embodiment, the target movement score may record whether the eye is within or outside of the range of a target as it moves, as opposed to distinguishing the type of eye movement characteristic. An individual's user score may then be graphed and compared to the amount of error between the performance curve and the criterion performance curve for the length of time of the task.

$$\text{target movement score} = \frac{\text{time on target}}{\text{total time}}$$

Smooth Pursuit Eye Movement Score:

In one embodiment, a smooth pursuit eye movement score may evaluate an error measure used for continuous skills, such as following a ball (or object) to indicate the amount of error between the performance curve and the criterion performance curve for a specific amount of time during which the performance is sampled. The smooth pursuit eye movement score may distinguish between the type of eye movement characteristic and only include smooth pursuit eye movements (i.e., excluding fixations or saccades). The smooth pursuit score may be calculated as follows:

$$\text{smooth pursuit score} = \frac{\text{time on target with smooth pursuit movement}}{\text{total time}}$$

The individual user's score may be graphed and compared to the amount of error between the performance curve and the criterion performance curve for the length of time of the task.

Decision Making Score:

In one embodiment, a decision making score may evaluate the participant's ability to make the correct decision regarding the outcome of the task. The decision making score may or may not be a combination of the response time score and accuracy of response associated with the outcome of the task. One example may be, to look to the right or left, high or low, to follow or not to follow a target (i.e. go or no-go) decision making. Metrics for the decision making score may or may not be binary (for example, 10 correct, 5 incorrect) and/or binary with response time (for example, 10 correct within 5 seconds).

Direction Score:

In one embodiment, a direction score may evaluate the ability of the participant to follow directions of the task. During a pre-task explanation and test, the score may evaluate whether the user followed the directions required to begin the task, such as whether a user looked at an object when asked to do so. The metrics for the direction score may or may not be binary "Yes" or "No", "Green light" or "Red Light," and they may or may not be a percentage of "readiness".

Recognition Score:

In one embodiment, a recognition score may be a score that indicates decision accuracy that includes but is not limited to verbal and/or motoric response, with reasoning, regarding where a subject should be looking and may or may not include temporal aspects of the task. In certain embodiments, the task may be static or dynamic, and the time may or may not be included in the metric. For example, the user may be required to verbally respond to the particular play (e.g. running play) in American football and then must explain why he recognizes the play as a running play. The recognition score may measure whether the athlete's response to the recognition of the play is accurate or inaccurate and the recognition score may or may not include a time to respond.

Cue Identification Score:

In one embodiment, a cue recognition score may indicate a decision accuracy that includes but is not limited to verbal and/or motoric response, without reasoning, regarding where a subject should be looking and may or may not include temporal aspects of the task. In one embodiment, a task may be static or dynamic, and time may or may not be included in the metric. For example, the user may be required to verbally respond to the particular play (e.g. running play) in American football. Unlike the recognition score, the user does not need to explain their reasoning for the decision to call what they saw as a "running play". The cue identification score may measure whether the user's response to the cue/display is accurate or inaccurate, and may or may not include a time to respond.

Reasoning Score:

In one embodiment, a reasoning score may evaluate a measure of a participant's quality to explain why he or she responded in a certain way to a task and/or a part of a task. A reasoning score may include looking at a location, and responding with a verbal and/or motor response. The reasoning score may provide information on what is being extrapolated and/or interpreted from the environment. One example may be a subject having to pick a "best response" from a list of responses and/or explanations. The reasoning score may be a qualitative measure or a quantitative measure.

Static Visual Acuity Score:

In one embodiment, a static visual acuity score may evaluate a participant's ability to observe stationary detail in varying contrast conditions. The static visual acuity score may be determined by a combination of accuracy in recognition and may or may not include time, angular velocities, and/or various contrast conditions. The static visual acuity score may represent an ability to find relevant information within a "busy" environment. The static visual acuity score can be used to determine an athlete's ability to detect essential information, accurately and efficiently within their environment. For instance, a quarterback in American football may need to determine within an instant, where his teammates are located and be able to follow them (visually) from one location to another. In one embodiment, a formula for the static visual acuity score may be:

$$\text{static visual acuity score} = \frac{\text{cue identification}}{\text{time to complete task}} \text{ or } \frac{\text{\# of cues identified}}{\text{time to complete task}}$$

Dynamic Visual Acuity Score:

In one embodiment, a dynamic visual acuity score may evaluate the participant's ability to observe detail while movement is occurring in varying contrast conditions. The dynamic visual acuity score may be determined by a combination of accuracy in recognition, and may or may not include time, angular velocities, and/or various contrast conditions. The dynamic visual acuity score may represent an ability to find relevant information within a "busy" environment, where objects are moving at varying speeds from various distances, and shapes and colors. The dynamic visual acuity score can be used to determine an athlete's ability to detect essential information accurately and efficiently within a changing environment. For instance, a quarterback in American football may need to determine within an instant, where his teammates are located. In one embodiment, a formula for the dynamic visual acuity score may be:

$$\text{dynamic visual accuity score} = \frac{\text{cue identification}}{\text{time to complete task}} \text{ or } \frac{\text{\# of cues identified}}{\text{time to complete task}}$$

Verbalization Score:

In one embodiment, a verbalization score may evaluate a qualitative or quantitative measure of the participant's verbal "self-talk" while engaging in a task. The metrics for this may or may not include length of utterance/time and/or the number of positive statements, the number of negative statements, and/or the number of corrective statements.

Breathing Score:

In one embodiment, a breathing score may be a measure of the participant's breath rate over time, breath holds, intake and outtake time, and/or temporal phasing of breath. The breath score may provide an indicator of stress and exertion during an activity. This may or may not be used in a correlational or causal fashion to further understand eye movement behaviors. In one embodiment, a breathing score may be calculated based on a rate of breath divided by an amount of time.

Visual Stability Score:

In one embodiment, a visual stability score may be the length of time a fixation or gaze location remains stable (within, for example, 3 degrees of visual angle for a minimum of 100 milliseconds) on a target in accordance with head tilt measured by the visual angle score. In one embodiment, a visual stability score may be calculated based on a fixation length divided by an amount of time.

Brain Plasticity Score:

In one embodiment, a brain plasticity score may evaluate the participant's capacity to change the structure and ultimately the function of the brain. Initial research indicates that during training exercises, gathering eye movements can be a useful indicator of brain plasticity. The brain plasticity score may be measured from one testing session to the next and may or may not be measured at increments between testing sessions. The brain plasticity score may be used to indicate a rate of change and adaptation based on in-task and related-to-task training tools recommended to the individual to be applied, including training games, video games, training drills and/or other training programs. The brain plasticity score may be measured via the change over time in the reasoning score and/or the recognition score and/or the target score.

Predicting Potential Score:

In one embodiment, a predicting potential score may be used to predict an individual's future level of competency in visual search. In one embodiment, a predicting potential score may be generated based on one or more of the above-described brain plasticity score, dynamic visual acuity score, decision making score, reaction time score, visual routine score, target score, cognitive load score, and/or stress potential indicator score. In one embodiment, the predicting potential score may represent potential "upside" or "downside" rates of the user. For example, an individual's potential for elite performance may be predicted using perceptual skills, including eye movement behavior, such that elite performers can be differentiated from less elite counterparts, even at a very early age. These scores and their related data metrics may be weighted based on the task and research results that help define their level of importance as a predictor of future performance.

In one embodiment, a predicting potential score may be calculated by defining the perceptual performance parameters of importance for the particular task, given that different tasks rely more heavily on certain parameters than others. For example, since reaction time may be important for baseball, the reaction time score may be included in the predicting potential score for baseball. Whereas, if reaction time is found to be less important for, e.g., golf, then reaction time may be omitted as a predicting potential indicator for that task.

Next, a predicting potential score may be calculated by determining a weight for each category of performance parameters deemed important for the task. For example, in baseball, it may be determined that the reaction time score and the decision making score are equally important indicators of predicting potential, and a third variable, e.g. the cue variable score, may be determined to be about half as important as the reaction time score in predicting potential. As a result, the cue variable score may be rated lower and in turn given a lower percentage in terms of the overall score. Thus, a predicting potential score for baseball might include, for example, a reaction time score weighted at 40 percent, a decision making score weighted at 40 percent, and a cue identification score weighted at 20 percent.

Next, an individual score may be calculated for each metric of importance for predicting potential for this task. For example, the reaction time score may be found to be 90%, the decision making score may be found to be 95%, and the cue identification score may be found to be 98%. Each component score may then be multiplied by the weight assigned above to that component. For example, if a user received a 90 percent as a reaction time score, which may have been weighted as 40 percent of the total grade, the method may include multiplying 0.90 by 0.40 to obtain 0.36, or 36 percent. This may be repeated for any other scores determined as being correlated to strong future performance in a particular task. Finally, a total weighted percentage may be calculated by adding the percentages for each category derived from the weighting. Thus, if the user received a 36 percent weighted reaction time score, a 38 percent weighted decision making score, and a 19.6 percent weighted cue identification score, then 36, 38, and 19.6 may be summed to obtain a weighted average of 93.6 percent.

In one embodiment, analysis of a predicting potential score may include determining where a user falls compared to a standardized group of peer norms. For example, a little league baseball player with a decision making score of 95% compared to a group of his peers may fall in the top 1% of all his peers. This process may continue until all relevant metrics for the task were scored and compared to metrics within the peer group norms. One exemplary result is reflected in the table below:

| Metric | Average Score | Weight (Level of importance for the task of baseball) | Weighted Percentage | Ranking Percentage (compared to peer group norms per score) | Ranking Percentage (compared to peer group norms to determine overall score) | |
|---|---|---|---|---|---|---|
| Reaction Time Score | 90% | 40% | 36% | Top 1% | .004 | .4 |
| Decision Making Score | 95% | 40% | 38% | Top 3% | .012 | 1.2 |
| Cue Identification Score | 98% | 20% | 19.6% | Top ½% | .001 | .1 |
| | | | 93.6% TOTAL | | TOTAL = | 1.7 |

In one embodiment, the predicting potential score may be calculated by multiplying the weighted percentage with the ranked percentage to determine the overall ranking percentage, as illustrated in the table above. In this case, the ranking percentage may be 1.7%, meaning that this user is in the top 1.7% of all people in his peer group for the predicting potential metrics for baseball. Thus, the overall ranking percentage of this individual may suggest that he or she is a "highly qualified" candidate, likely to become an elite baseball player in terms of the perceptual-motor skills important for performing the task.

Blink Score:

In one embodiment, a blink score may refer to the timing and/or length of a blink before and/or during and/or after a task. The blink score may provide information about "lost" vision including when that vision was lost within the task which may help to indicate a loss of ball tracking at a critical point in time. In one embodiment, a formula for the blink score may include a time length of blinks divided by a length of a task.

Blind Vision Score:

In one embodiment, a blind vision score may be generated when the eye is tracking an object which may or may not change distances and/or speeds. For example, blind vision may occur when the eye can no longer physiologically track the object due to either the distance and/or speed of the object. The score may be presented as a percentage, a raw score, a time score, and/or an "off"/"on" score. In one embodiment, a possible formula for the blind vision score may include a time that an eye is "on," i.e., tracking, divided by a total task time.

Visual Inhibition Score:

In one embodiment, a visual inhibition score may evaluate the ability of the participant to not move the eye toward an object. This score may be reported as a binary "yes/no" score and/or a score based on overall number of inhibitions during a specific task. The visual inhibition score may be important as an indicator of distractibility and impulse control.

Task Parameter Information:

In one embodiment, task parameter information may include various aspects of the task at hand, including distance, speed, velocity, angles, heights etc. Task parameter information may be relevant scientific information, including but not limited to physics, biomechanics, perceptual-motor, mathematical, neuro-scientific, physical, etc. on what is required in order to affect a performance.

As discussed above, eye evaluation system 110 may calculate any number or combination of the above scores based on information collected from wearable cameras 104, remote cameras 106, and/or network resources 112. Eye evaluation system 110 may calculate any number or combination of the above scores based on the exemplary formulas described above, and incorporate any of the above scores in calculating one or more of the target score, the cognitive load score, and/or the stress indicator score. Numerous other scores may be generated over time based on task additions, eye movement characteristics, eye movement behaviors and/or additional tools added to eye movements, including, for example, psycho-physiological monitoring, biofeedback and/or biomechanical tools, and/or biometrics, such as EEG and heart rate.

Any of the above described scores may be measured based on any number of performance and/or learning metrics. For example, notwithstanding the exemplary formulas described above, any of the formulas may be adjusted and the scores therefore calculated, based on any of the following physical measurements, including: velocity data (rate of change of an object's position over time), acceleration (change in velocity during a movement, derived by dividing change in velocity by change in time), displacement (change in spatial position during the course of a movement), kinematics (motion without regard to the force or mass), linear and angular motion, force, mass, degrees of change, degrees of visual angle, distance, number of trials, length of trials, time (time of a task, reaction time, response time, movement time, etc.)

In addition, any of the scores may be calculated based on characteristics of the participant(s), including parameters such as: coordination, practice, competition, fatigue, motivation, retention, vigilance, monocular or binocular, central (focal) or peripheral vision, psychological refractory period, stage of learning (e.g. cognitive stage, associative stage, autonomous stage, etc.), diversification (e.g., the learner's ability to acquire the capability to modify the movement pattern according to environmental characteristics), transfer of learning (positive or negative), and training (e.g., length, time, frequency, quality).

In addition, formulas and scores may be adjusted based on statistical metrics: qualitative statistics, quantitative statistics, error scores (e.g., constant error, absolute error, variable error, root mean squared error), arithmetic (e.g., summing, subtracting, dividing, multiplying), standard deviations, raw score/data, statistical significance, statistical power, and so on. Further statistical testing may include but not be limited to T-Tests, analysis of variance (ANOVA), repeated analysis of variance, Wilcoxon-Mann-Whitney test, chi-square test, regression, Freidman test, correlational analysis, discriminate analysis, multivariate analysis of variance (MANOVA), and/or Cronbach alpha. In addition, formulas and scores may be adjusted based on eye movement metrics, such as biofeedback measures, psycho-physiologicial measures, biomechanical measures, environmental and/or biometric measures, among others.

As described above, any of the scores or other information generated by eye evaluation system 110 may be presented electronically, such as by transmission to client devices 108. For example, in one embodiment, eye evaluation system 110 may report data to clients or customers of the entity operating eye evaluation system 110 in the form of one or more reports. Data reporting may include, but not be limited to one or more of the following: single user reports, group reports (more than one user), reports across multiple groups, a single report alongside a group report, a report of skill level for individual users and/or groups, a report of any number of demographic variables to include but not limited to age and/or gender reports, environmental condition reports, longitudinal reports of individuals and/or groups over more than one data input session, a report of any eye movement characteristics and/or behaviors for a user and/or group, a report of any psycho-physiological and/or biofeedback and/or biomechanical and/or biometric tool and/or environmental conditions with or without eye movement data, a quantitative and/or qualitative report, a report with or without video footage, images, scores, training recommendations, temporal phases, and/or graphical representations (e.g., bar charts, line graphs, pie charts).

In one embodiment, a report may include, but be not limited to: comparison of data, displaying data, interacting with data, collating data, raw data displays, quantifying data beyond raw output (e.g., summing, averaging, percentiles, angles, etc.), further data analysis (e.g., variance, effect sizes, t-tests, co-efficient, degrees of freedom, video, images, scores, displaying graphics, etc.).

Figure 7:
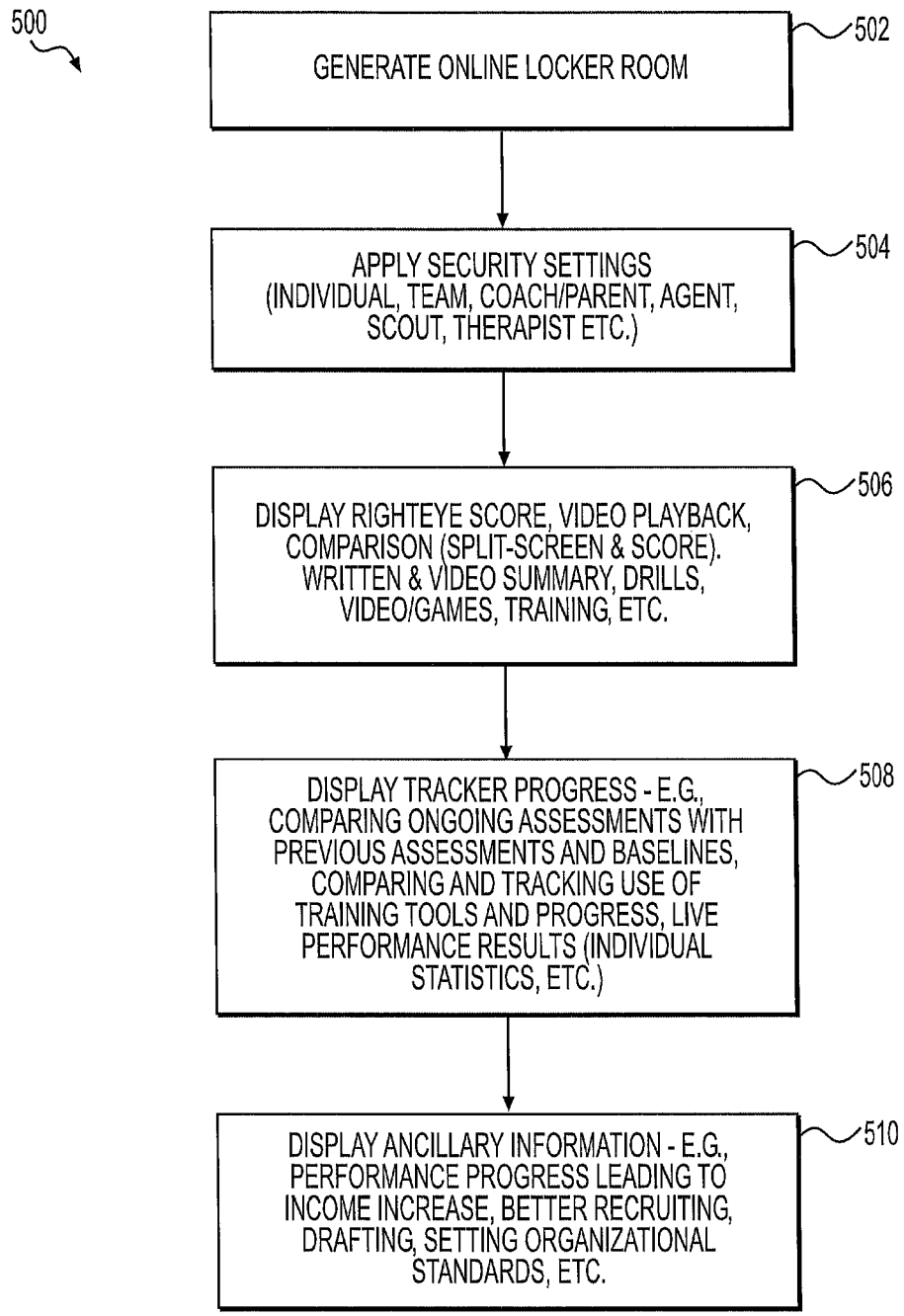
FIG. 7 is a flow diagram of another exemplary method for displaying evaluations of individuals' eye movements and recommended training tasks for individuals to improve their visual search and other eye movements, according to an exemplary embodiment of the present disclosure.

FIG. 7 is a flow diagram of another exemplary method for displaying evaluations of individuals' eye movements and recommended training tasks for individuals to improve their visual search and other eye movements, according to an exemplary embodiment of the present disclosure. Specifically, FIG. 7 depicts a method 500 for displaying one or more of the above calculated scores to participants and/or participants' employers, such as to client devices 108. As shown in FIG. 7, method 500 may include generating an online "locker room" (step 502). Of course, a "locker room" may be any type of online user account, and may include any alternative naming convention based on the type of participant that the operator of eye evaluation system 110 is catering to. Generating the online account may include establishing web servers in communication with eye evaluation system 110, granting access to databases of scores and information, and establishing user interfaces for receiving, viewing, and interacting with stored scores and data. Method 500 may also include applying security settings (step 504). For example, access to the online account (or "locker room") may be controlled at the individual (participant) level, team level, by coaches and/or parents, agents, scouts, therapists, employers, etc.

In one embodiment, method 500 may include displaying at a client device 108 the one or more calculated scores, such as the generated target score, cognitive load score, and/or stress indicator score (one or more of which may be referred to as a proprietary "RightEye Score") (step 506). For example, eye evaluation system 110 may display one or more scores along with a video playback of the evaluated action or task, comparisons to other individuals, written and/or video summaries of analysis, recommended training drills, video or game training drills, etc., of any of the other generated information discussed above with respect to the methods of FIGS. 3-6. Method 500 may also include displaying tracking progress (step 508), which may include comparing ongoing assessments with previous assessments and baselines, comparing and tracking use of training tools and progress, and displaying live performance results (e.g., individual statistic). For example, method 500 may include displaying the results of performing comparisons (as in step 208, FIG. 3), recommending training (as in steps 210, 212, FIG. 3), and reassessing/testing (as in step 214, FIG. 3). Method 500 may also include displaying ancillary information (step 510), such as performance progress leading to income increase, better recruiting, better drafting, meeting organizational standards, etc. Thus, method 500 may display any of the results from performing the methods of FIG. 3-6, and related information about how those methods improve the visual search and performance of its participants.

Figure 8:
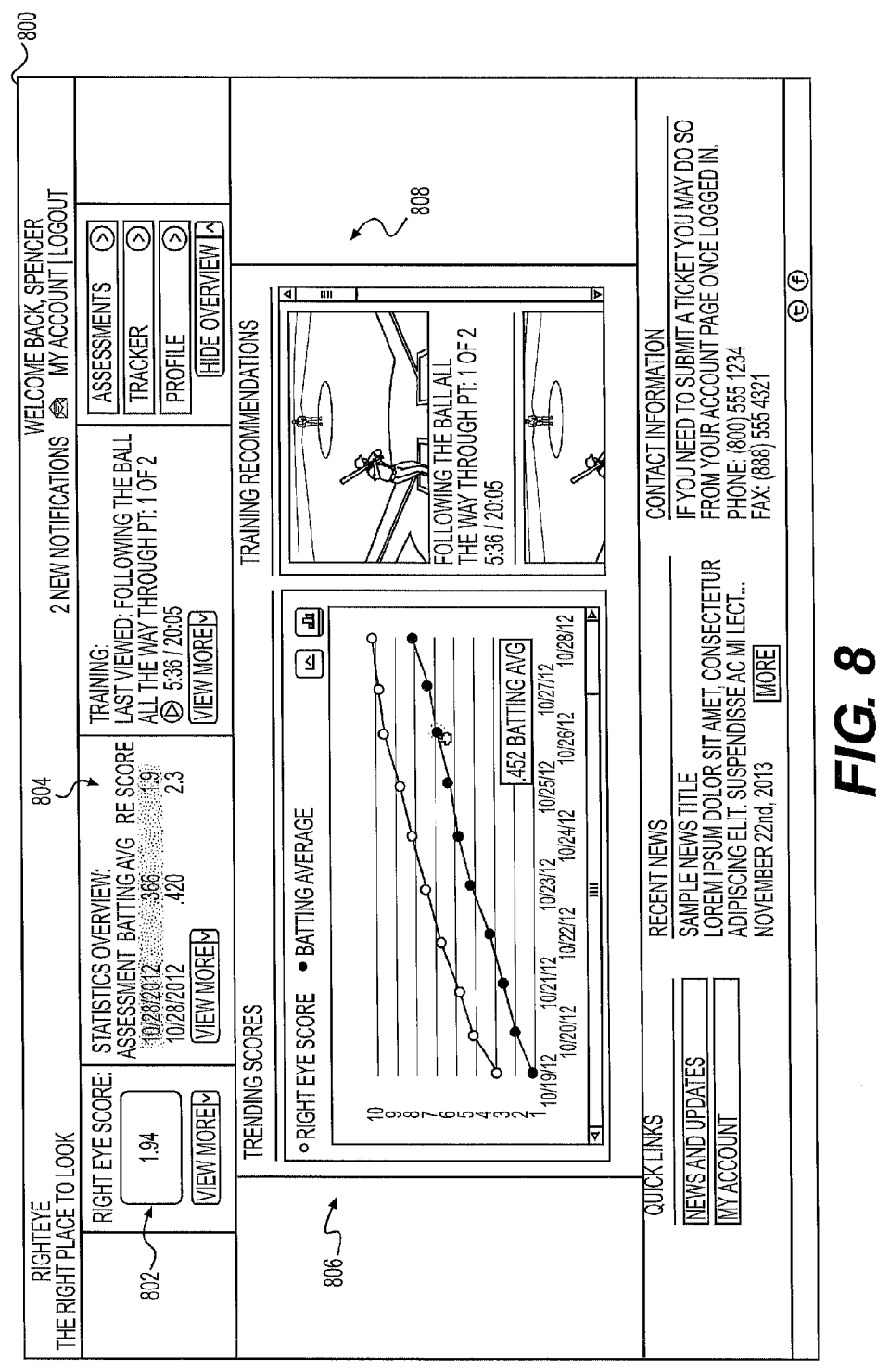

FIG. 8 is a schematic diagram of an exemplary display of evaluations of individuals' eye movements and recommended training tasks for individuals to improve their visual search and other eye movements, according to an exemplary embodiment of the present disclosure. In one embodiment, FIG. 8 is a screenshot of a web-based interface 800 for interacting with eye evaluation system 110. Web-based interface 800 may be managed or operated by eye evaluation system 110, hosted on one or more web servers over the Internet, and displayed on one or more client devices 108.

In one embodiment, web-based interface 800 displays various eye evaluation information, such as various scores and information calculated according to the methods of FIGS. 3-6. For example, web-based interface 800 may display a proprietary RightEye Score 802, which may be or include one or more of the target score, cognitive load score, and/or stress indicator score generated according to the methods described above. Web-based interface 800 may also display statistics associated with an evaluated task 804, such as how a participant's performance may vary over time, and how a proprietary eye evaluation score may correlate with other scores or statistics typical of the evaluated task. In this case, web-based interface 800 depicts a calculated eye evaluation score in relation to a batting average calculated on different days. Although web-based interface 800 depicts the display of eye evaluation information in relation to baseball statistics, it should be appreciated that the web-based interface 800 may display eye evaluation information in relation to any other information or statistics typical of any other sport, activity, or profession, depending on the task and/or the participant. As shown in FIG. 8, the web-based interface 800 may also depict an eye evaluation score in a graph 806, along with one or more task-specific metrics or statistics, in this case batting average, over time. The web-based interface 800 may also display one or more training recommendations 808, such as any of the training recommendations generated in steps 210, 212 (FIG. 3). For example, web-based interface 800 may display training videos, embed training games, or display descriptions of how to improve visual search and/or techniques for improving any of the eye evaluation scores described above.

Figure 9:
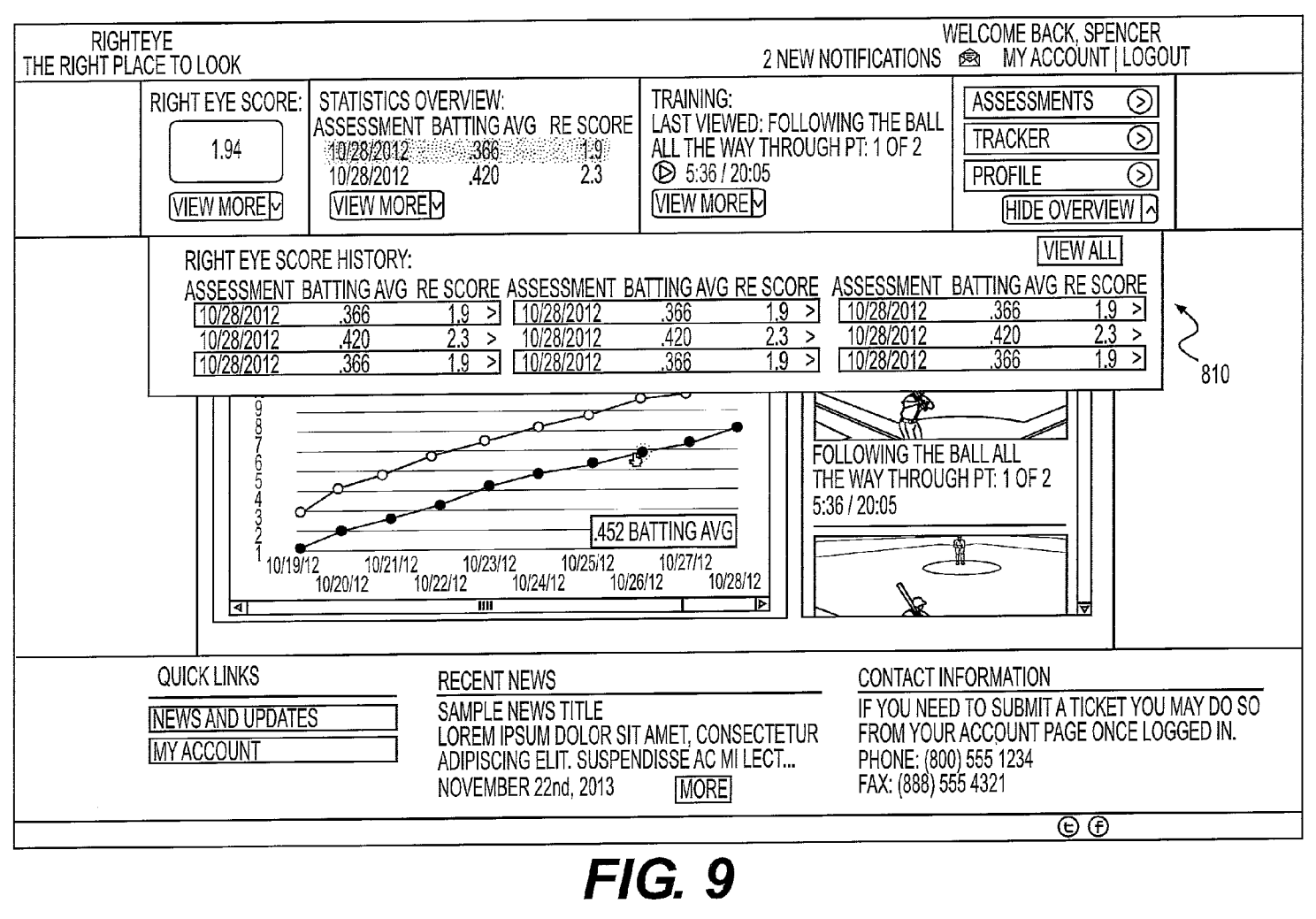

FIG. 9 is a schematic diagram of the exemplary display of evaluations of individuals' eye movements and recommended training tasks of FIG. 8, but also including a display of history 810 of a participant's eye evaluation scores and task-specific scores or metrics.

Figure 10:
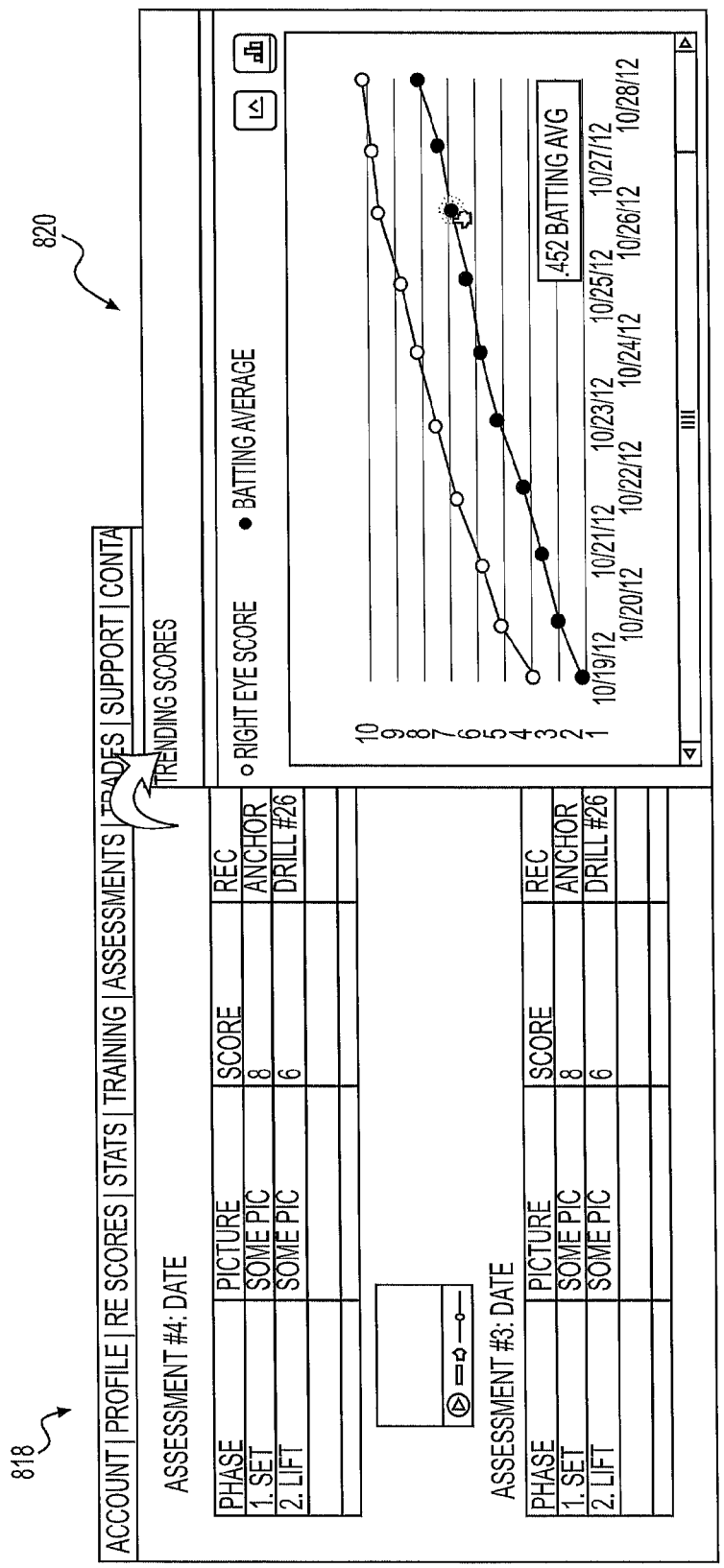
FIG. 10 is a schematic diagram of an exemplary display of evaluations of individuals' eye movements and recommended training tasks for individuals to improve their visual search and other eye movements, according to an exemplary embodiment of the present disclosure.

FIG. 10 is a schematic diagram of an exemplary display of evaluations of individuals' eye movements and recommended training tasks for individuals to improve their visual search and other eye movements, according to an exemplary embodiment of the present disclosure. As shown in FIG. 10, the web-based interface 800 of FIG. 8 may include an assessment page 818, including a breakdown of temporal or biometric phases, related pictures, related eye evaluation scores, and recommend drills. The assessment page 818 may also include links for participants to view and modify account information, profile information, eye evaluation scores, training, assessments, trades, and support. In addition, the assessment page 818 may include a trending scores window 820. Trending scores window 820 may graph one or more eye evaluation scores in relation to a task-specific score or metric over time, in this case graphing batting average against an eye evaluation score over time.

Figure 11:
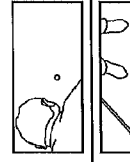
FIG. 11 is a schematic diagram of an exemplary display of evaluations of individuals' eye movements and recommended training tasks for individuals to improve their visual search and other eye movements, according to an exemplary embodiment of the present disclosure.

FIG. 11 is a schematic diagram of another exemplary embodiment of the assessment page 818 of FIG. 10. As shown in FIG. 11, the assessment page may depict a plurality of static phases 826, including preparation, back swing, down swing, contact, and finish. The assessment page may also depict one or more related images 828, which may be images of the participant involved in the respective static phase, or of a professional or expert in an ideal stage of movement. The assessment page may also depict an eye evaluation score 830 associated with each static phase. Finally, the assessment page may depict a training recommendation 832 in relation to each static phase. As discussed above, a training recommendation may be automatically selected based on a library of possible training recommendations corresponding to different scores. For example, a training recommendation may be made based on whether it statistically improved the eye movement of others with similar eye evaluations or score.

Figure 12:
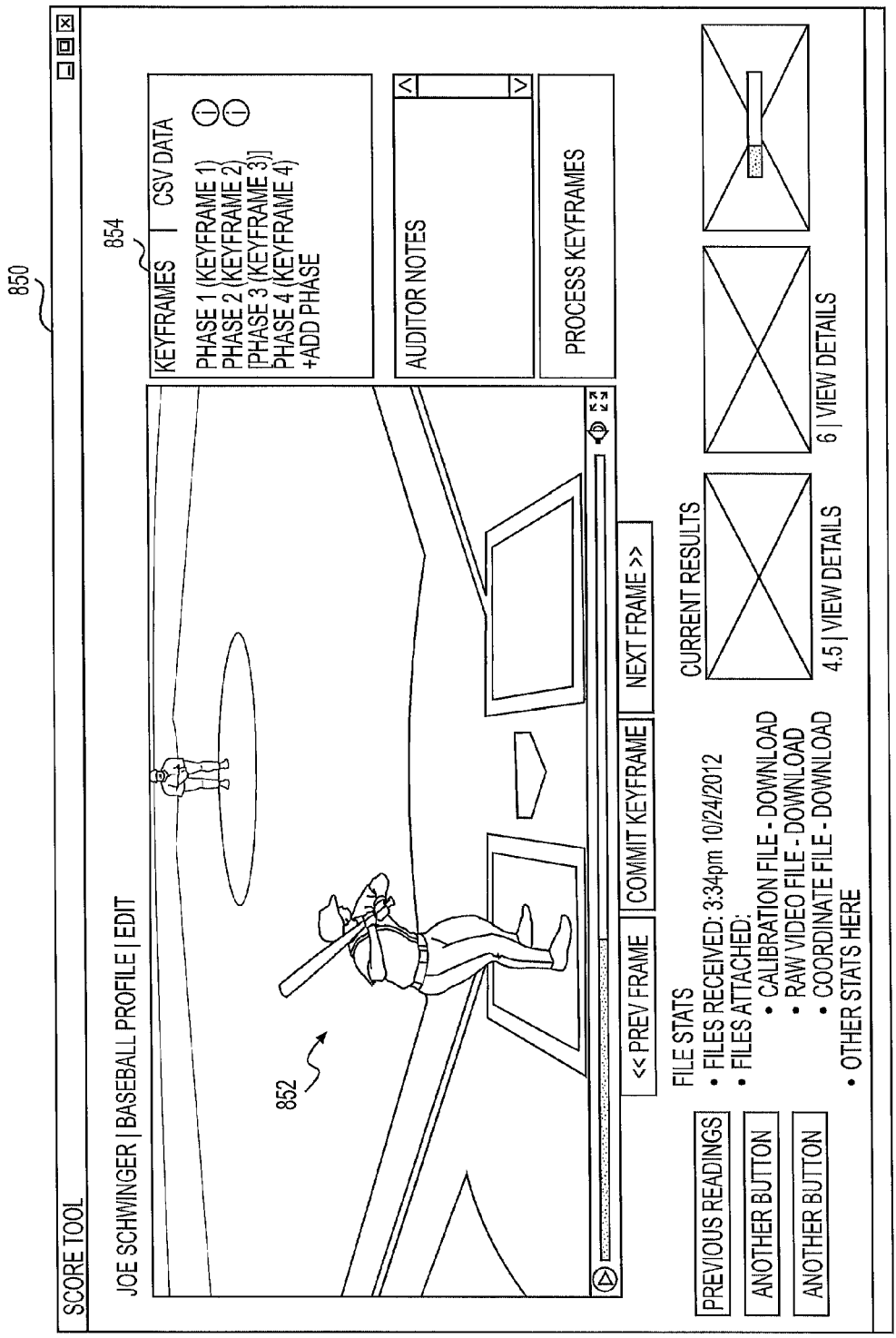
FIG. 12 is a schematic diagram of an exemplary display of evaluations of individuals' eye movements and recommended training tasks for individuals to improve their visual search and other eye movements, according to an exemplary embodiment of the present disclosure.

FIG. 12 is a schematic diagram of an exemplary display of evaluations of individuals' eye movements and recommended training tasks for individuals to improve their visual search and other eye movements, according to an exemplary embodiment of the present disclosure. Specifically, FIG. 12 shows that web-based interface 800 may include a scoring tool 850, which may include a video 852 embedded therein of a participant engaged in an evaluated task. In one embodiment, the scoring tool 850 may include keyframe data 854 enabling a user to evaluate the video 852 and define certain temporal phases (e.g., phase 1, phase 2, etc. as shown), for purposes of defining video segments and enclosed eye movement for scoring according to the methods of FIGS. 3-6.

Figure 13:
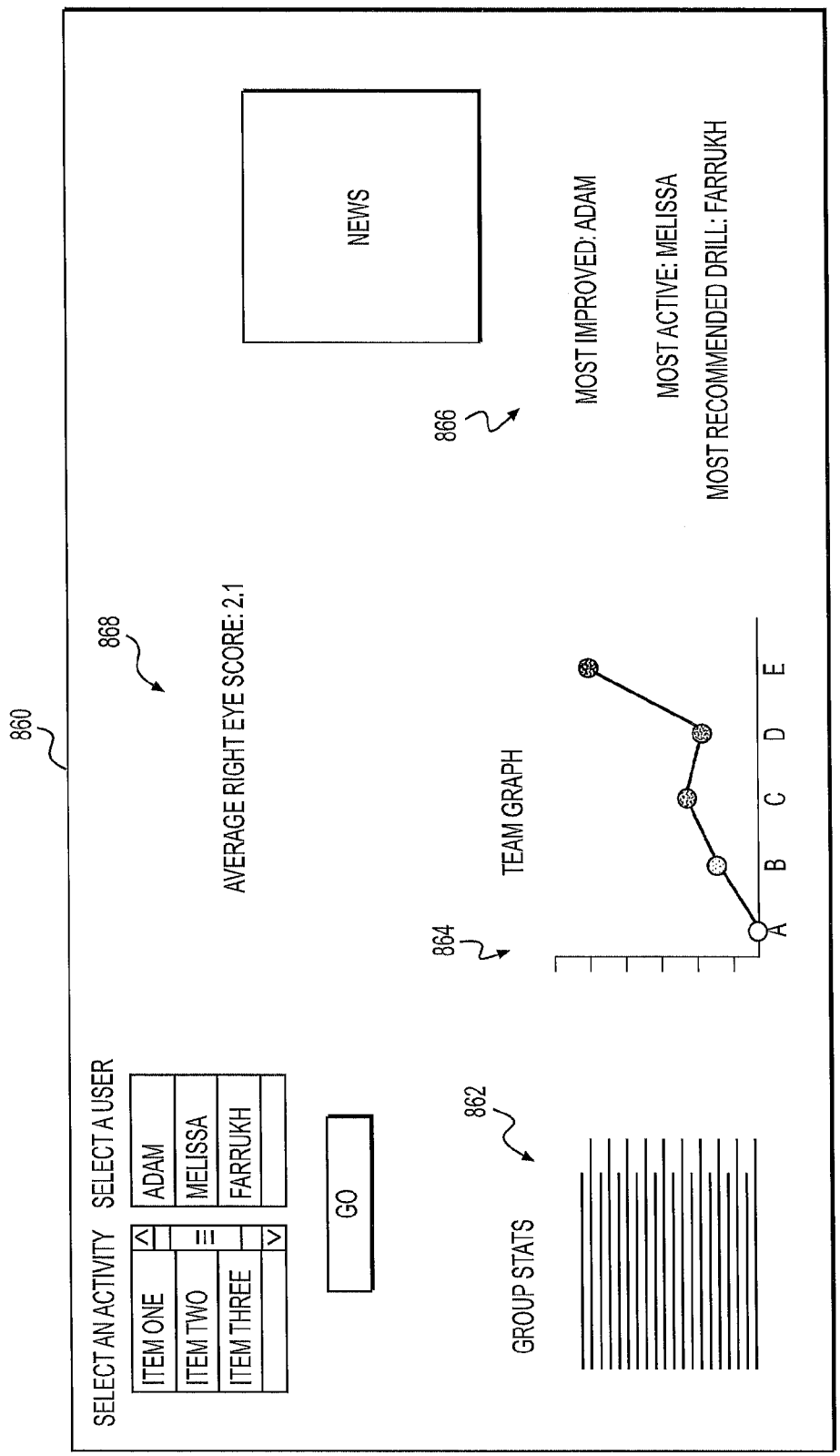
FIG. 13 is a schematic diagram of an exemplary display of evaluations of individuals' eye movements and recommended training tasks for individuals to improve their visual search and other eye movements, according to an exemplary embodiment of the present disclosure.

FIG. 13 is a schematic diagram of another exemplary display of evaluations of individuals' eye movements and recommended training tasks for individuals to improve their visual search and other eye movements. Specifically, FIG. 13 depicts a team window 860 of web-based interface 800. As shown in FIG. 8, team window 860 may display one or more group stats 862 associated with a team, such as statistics relating to one or more eye evaluation scores averaged across the team. Team window 860 may also display a team graph 864, which may graph one or more of the above described scores as averaged across a team over time or across team members. Team window 860 may also depict information 866 on specific team members relative to the whole team, such as "most improved," "most active," or "most recommended drill." Team window 860 may also display an average eye evaluation score 868 for an entire team. Of course, the average eye evaluation score may be of the target score, cognitive load score, and/or stress indicator score, or any other ancillary score described above, as averaged across one or more members of a team.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims,

What is claimed is:

1. A computer-implemented method comprising:
receiving data representing a location where an individual's eye or eyes are looking before, during, or after the individual performs a task involving movement of the individual relative to a physical environment;
identifying a visual cue of where the individual should be looking during the task, at a point in the physical environment that is associated with the individual or an object during a biomechanical phase of the individual, the visual cue being identified based on performance of the task by one or more other individuals;
generating a score of a location where the individual's eye or eyes are looking relative to the location of the visual cue during the biomechanical phase of the individual, based on analysis of the received data relative to the visual cue;
generating an electronic display for informing the individual of the location of the visual cue and recommending training for the individual to perform based on the location of the visual cue;
receiving data representing a location where the individual's eye or eyes are looking before, during, or after the individual performs second or subsequent iterations of the task; and
updating the score or generating a new score based on locations where the individual's eye or eyes are looking relative to the location of the visual cue during biomechanical phases of the individual involved in the second or subsequent iterations of the task.

2. The method of claim 1, wherein the data is one or more of: image data of the individual's eye or eyes, coordinate data of the location of the individual's eye or eyes, and coordinate data of a location on which the individual's eye or eyes were looking.

3. The method of claim 1, wherein the data is received, either locally or over a network, from a wearable eye tracker configured to obtain the data by imaging the individual's eye or eyes.

4. The method of claim 1, further comprising:
determining a target range associated with the visual cue, the target range defining a viewing area around the visual cue; and
generating a score of the location where the individual's eye or eyes are looking by scoring where the individual's eye or eyes are looking relative to the determined target range.

5. The method of claim 1, further comprising:
identifying movement of the identified visual cue, the identified movement including a set of coordinates of the visual cue at each of a plurality of points in time; and
determining a target range associated with each of the sets of coordinates of the visual cue.

6. The method of claim 1, wherein generating an electronic display for recommending training for the individual to perform based on the location of the visual cue, includes recommending one or more training drills to the individual based on the score.

7. The method of claim 1, wherein generating the score of the location where the individual's eye or eyes are looking includes one or more of: generating a target score, generating a cognitive load score, and calculating a stress indicator score.

8. The method of claim 7, wherein generating the score includes generating the target score, and wherein the target score is generated based on a bull's-eye arrangement centered around the visual cue.

9. The method of claim 7, wherein generating the score includes generating the cognitive load score, and wherein the cognitive load score is generated based on a number of eye shift movements detected within an interval of time.

10. The method of claim 7, wherein generating the score includes generating the stress indicator score, and wherein the stress indicator score is calculated as the sum of the target score and the cognitive load score.

11. The method of claim 1, further comprising calculating a potential score that is predictive of the individual's performance in the task, as a function of one or more parameters identified as predictive of future performance in the task.

12. The method of claim 1, further comprising:
calculating a score for each of the one or more parameters predictive of future performance in the task;
determining a weight for each of the one or more parameters; and
calculating a total potential score based on the determined weights and the calculated scores.

13. A system comprising:
a data storage device storing instructions for evaluating human eye movement;
a processor configured to execute the instructions to perform a method including:
receiving data representing a location where an individual's eye or eyes are looking before, during, or after the individual performs a task involving movement of the individual relative to a physical environment;
identifying a visual cue of where the individual should be looking during the task, at a point in the physical environment that is associated with the individual or an object during a biomechanical phase of the individual, the visual cue being identified based on performance of the task by one or more other individuals;
generating a score of a location where the individual's eye or eyes are looking relative to the location of the visual cue during the biomechanical phase of the individual, based on analysis of the received data relative to the visual cue;
generating an electronic display for informing the individual of the location of the visual cue and recommending training for the individual to perform based on the location of the visual cue;
receiving data representing a location where the individual's eye or eyes are looking before, during, or after the individual performs second or subsequent iterations of the task; and
updating the score or generating a new score based on locations where the individual's eye or eyes are looking relative to the location of the visual cue during biomechanical phases of the individual involved in the second or subsequent iterations of the task.

14. The system of claim 13, wherein the data is one or more of: image data of the individual's eye or eyes, coordinate data of the location of the individual's eye or eyes, and coordinate data of a location on which the individual's eye or eyes were looking.

15. The system of claim 13, wherein the data is received, either locally or over a network, from a wearable eye tracker configured to obtain the data by imaging the individual's eye or eyes.

16. The system of claim 13, wherein the processor is further configured for:
determining a target range associated with the visual cue, the target range defining a viewing area around the visual cue; and
generating a score of the location where the individual's eye or eyes are looking by scoring where the individual's eye or eyes are looking relative to the determined target range.

17. The system of claim 13, wherein the processor is further configured for:
identifying movement of the identified visual cue, the identified movement including a set of coordinates of the visual cue at each of a plurality of points in time; and
determining a target range associated with each of the sets of coordinates of the visual cue.

18. The system of claim 13, wherein generating an electronic display for recommending training for the individual to perform based on the location of the visual cue, includes recommending one or more training drills to the individual based on the score.

19. The system of claim 13, wherein generating the score of the location where the individual's eye or eyes are looking includes one or more of: generating a target score, generating a cognitive load score, and calculating a stress indicator score.

20. A non-transitory computer readable medium storing instructions that, when executed by a computer, cause the computer to perform a method comprising:
receiving data representing a location where an individual's eye or eyes are looking before, during, or after the individual performs a task involving movement of the individual relative to a physical environment;
identifying a visual cue of where the individual should be looking during the task, at a point in the physical environment that is associated with the individual or an object during a biomechanical phase of the individual, the visual cue being identified based on performance of the task by one or more other individuals;
generating a score of a location where the individual's eye or eyes are looking relative to the location of the visual cue during the biomechanical phase of the individual, based on analysis of the received data relative to the visual cue;
generating an electronic display for informing the individual of the location of the visual cue and recommending training for the individual to perform based on the location of the visual cue;
receiving data representing a location where the individual's eye or eyes are looking before, during, or after the individual performs second or subsequent iterations of the task; and
updating the score or generating a new score based on locations where the individual's eye or eyes are looking relative to the location of the visual cue during biomechanical phases of the individual involved in the second or subsequent iterations of the task.

* * * * *